US011104966B2

(12) United States Patent
Ozanich et al.

(10) Patent No.: US 11,104,966 B2
(45) Date of Patent: Aug. 31, 2021

(54) SPENT ENRICHMENT MEDIA FOR GROWTH OF GENE-MATCHED MICROORGANISMS

(71) Applicant: Battelle Memorial Institute, Richland, WA (US)

(72) Inventors: Richard M. Ozanich, Richland, WA (US); Janine R. Hutchison, Richland, WA (US); Kristin D. Victry, Richland, WA (US); Becky M. Hess, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 222 days.

(21) Appl. No.: 16/131,524

(22) Filed: Sep. 14, 2018

(65) Prior Publication Data

US 2019/0002962 A1    Jan. 3, 2019

Related U.S. Application Data

(62) Division of application No. 14/742,367, filed on Jun. 17, 2015, now Pat. No. 10,100,369.

(60) Provisional application No. 62/013,998, filed on Jun. 18, 2014.

(51) Int. Cl.

| | |
|---|---|
| C12Q 1/68 | (2018.01) |
| C12Q 1/689 | (2018.01) |
| C12N 1/20 | (2006.01) |
| C07K 14/195 | (2006.01) |
| C12R 1/01 | (2006.01) |

(52) U.S. Cl.
CPC ............ *C12Q 1/689* (2013.01); *C07K 14/195* (2013.01); *C12N 1/20* (2013.01); *C12N 1/205* (2021.05); *C12R 2001/01* (2021.05)

(58) Field of Classification Search
None
See application file for complete search history.

(56) References Cited

U.S. PATENT DOCUMENTS 7,935,804 B2 * 5/2011 Dubensky, Jr. ..... A61K 39/0011
536/23.7

OTHER PUBLICATIONS

Obata et al. (Int J of Antimicrobial Agents, 2006, vol. 27, 32-39) (Year: 2006).*
Garcia et al. (Bioresource Technology, 2011, vol. 102, 7249-7256) (Year: 2011).*
Lowe et al. (Nucleic Acids Research, 1990, 18(7):1757-1761) (Year: 1990).*
Finkel et al. (Journal of Bacteriology, 2001, 183(21):6288-6293) (Year: 2001).*
Fong et al. (Infectand Immun, 2001, 69(12):7625-7634).*
Cheung et al., "The VirR Response Regulator from *Clostridium perfringens* Binds Independently to Two Imperfect Direct Repeats Located Upstream of the pfoA Promoter," *J. Bacteriol.*, vol. 182:57-66, 2000.
Herbert and Foster, "Starvation survival in *Listeria monocytogenes*: characterization of the response and the role of known and novel components," *Microbiology* 147:2275-2284, 2001.
Jonquières et al., "The inlA Gene of *Listeria monocytogenes* LO28 Harbors a Nonsense Mutation Resulting in Release of Internalin," *Infect Immun* 66(7):3420-3422, 1998.
Kim et al., "Isolation of Uncultivable Anaerobic Thermophiles of the Family of *Clostridiaceae* Requiring Growth-Supporting Factors," *J. Microbiol. Biotechnol.*, vol. 18:611-615, 2008.
Kim and Bhunia, "SEL, a Selective Enrichment Broth for Simultaneous Growth of *Salmonella enterica*, *Escherichia coli* O157:H7, and *Listeria monocytogenes*," *Appl. Environ. Microbiol.*, vol. 74:4853-4866, 2008.
Knabel, "Optimized, One-Step, Recovery-Enrichment Broth for Enhanced Detection of *Listeria monocytogenes* in Pasteurized Milk and Hot Dog," *J. AOAC Inter.*, vol. 85:501-504, 2002.
Lathrop et al., "Differential Expression of InlB and ActA in *Listeria monocytogenes* in Selective and Nonselective Enrichment Broths," *J. Appl. Microbiol.*, vol. 104:627-639, 2008.
Obata et al., "Association of rpoB Mutations with Rifampicin Resistance in *Mycobacterium avium*," *Int. J. Antimicrob. Agents*, vol. 27:32-39, 2006.
Olier et al., "Assessment of the pathogenic potential of two *Listeria monocytogenes* human faecal carriage isolates," *Microbiology* 148:1855-1862, 2002.
Ryser et al., "Recovery of Different *Listeria* Ribotypes from Naturally Contaminated, Raw Refrigerated Meat and Poultry Products with Two Primary Enrichment Media," *Appl. Environ. Microbiol.*, vol. 62:1781-1787, 1996.
Sun and Zhang, "Spent Culture Supernatant of *Mycobacterium tuberculosis* H37Ra Improves Viability of Aged Cultures of This Strain and Allows Small Inocula to Initiate Growth," *J Bacteriol* 181:7626-7628, 1999.
Tanaka et al., "*Catellibacterium nectariphilum* gen. nov., sp. nov., which Requires a Diffusible Compound from a Strain related to the genus *Sphingomonas* for Vigorous Growth," *Int. J. Syst. Evol. Microbiol.*, vol. 54:955-959, 2004.
Témoin et al., "Multiple point mutations in virulence genes explain the low virulence of *Listeria monocytogenes* field strains," *Microbiology* 154:939-948, 2008.
Vartoukian et al., "Strategies for Culture of 'Unculturable' Bacteria," *FEMS Microbiol. Lett.*, vol. 309:1-7, 2010.

(Continued)

*Primary Examiner* — Stephanie K Mummert
(74) *Attorney, Agent, or Firm* — Klarquist Sparkman, LLP

(57) ABSTRACT

A method for amplifying and detecting microorganisms, such as species of *Listeria*, is described. The method utilizes gene-matched enrichment media and PCR-based detection. The enrichment media is spent media produced using a modified microorganism containing a plurality of mutations in a selected gene such that the modified microorganism does not contain the PCR signature. Thus, PCR detects only the amplified microorganism of interest, not the modified microorganism. Exemplary methods and kits for amplification and detection of *Listeria* species are described.

**18 Claims, 3 Drawing S

(56) References Cited

OTHER PUBLICATIONS

Figure 1:
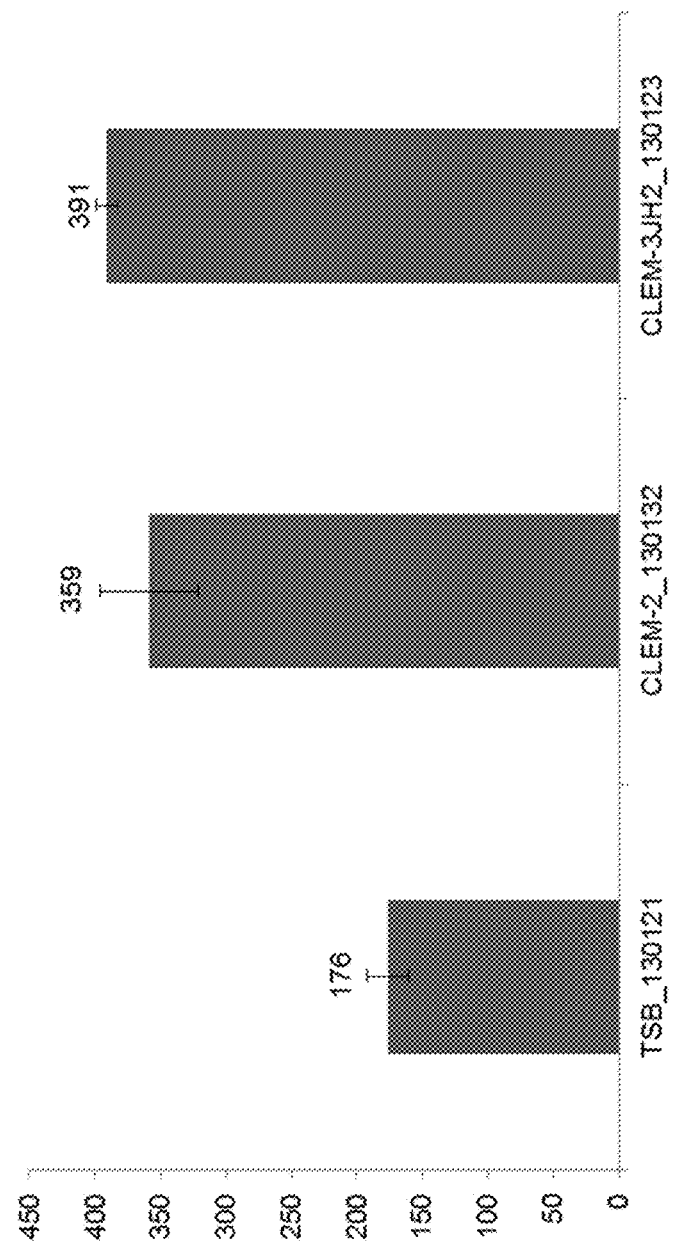
Figure 2:
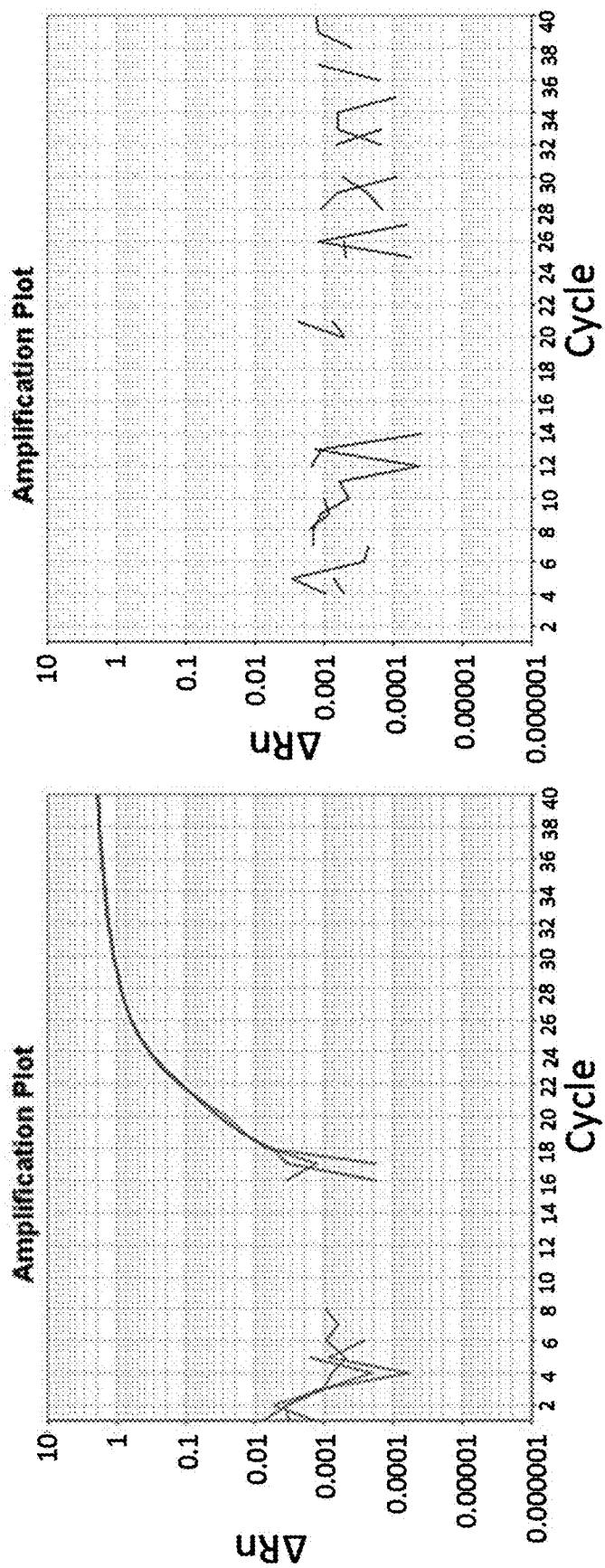
Figure 3:
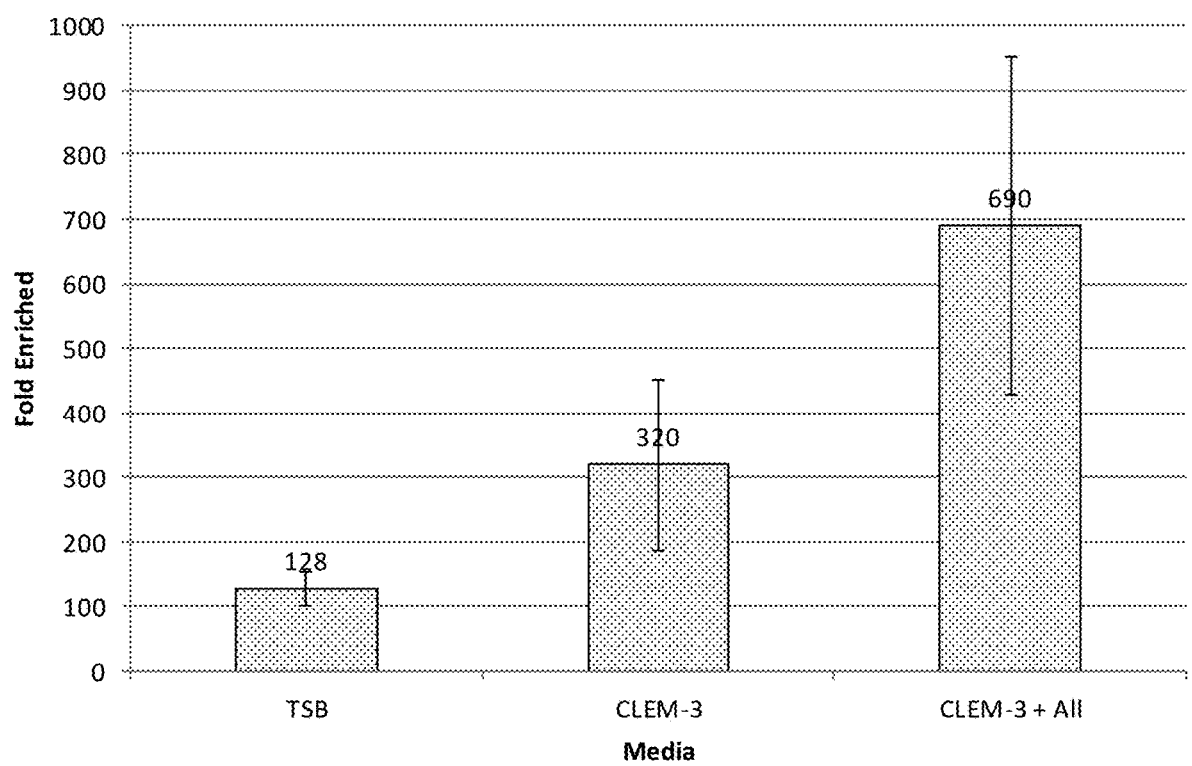

Waters and Bassler, "Quorum Sensing: Cell-to-Cell Communication in Bacteria," *Annu. Rev. Cell Dev. Biol.*, vol. 21:319-346, 2005.
Yang et al., "Conditioned Medium from *Listeria innocua* Stimulates Emergence from a Resting State: Not a Response to *E. coli* Quorum Sensing Autoinducer AI-2," *Biotechnol. Prog.*, vol. 22:387-393, 2006.
Uyttendaele et al., "Detection of *Campylobacter jejuni* Added to Foods by Using Combined Selective Enrichment and Nucleic Acid Sequence-Based Amplification (NASBA)," *Appl. Environ. Microbiol.*, vol. 6:1341-1347, 1995.
ThermoFisher Scientific, "Guidelines to Maintain Cultured Cells," retrieved from https://www.thermofisher.com/us/en/home/references/gibco-cell-culture-basics/cell-culture-protocols/maintaining-cultured-cells.html on or before Mar. 5, 2021, 3 pages.

* cited by examiner

SPENT ENRICHMENT MEDIA FOR GROWTH OF GENE-MATCHED MICROORGANISMS

CROSS REFERENCE TO RELATED APPLICATIONS

This application is a divisional of U.S. application Ser. No. 14/742,367, filed Jun. 17, 2015, which claims the benefit of U.S. Provisional Application No. 62/013,998, filed Jun. 18, 2014. The above-listed applications are herein incorporated by reference in their entirety.

ACKNOWLEDGMENT OF GOVERNMENT SUPPORT

This invention was made with government support under Contract DE-AC05-76RL01830 awarded by the U.S. Department of Energy. The government has certain rights in the invention.

FIELD

This disclosure concerns rapid detection of microorganisms, such as pathogenic microorganisms. This disclosure further concerns gene-matched enrichment media, kits containing such media, isolated nucleic acid molecules, and molecular detection of microorganisms.

BACKGROUND

Rapid detection of pathogenic organisms is important in many applications, including food safety, clinical diagnostics, homeland security and defense. The Centers for Disease Control and Prevention estimates that bacterial infections result in 99,000 deaths a year in the United States, at a cost exceeding $10 billion. Standard methods for identification of bacteria require 24-48 hours and utilize traditional enrichment media and selective culturing on agar plates. While some recent methods have achieved 8-hour detection times for fast growing bacteria such as *Escherichia coli*, most bacterial species require much longer enrichment times to achieve adequate cell replication to enable accurate detection.

Food processors test large numbers of samples from food processing equipment surfaces, ingredients, raw food and finished product. Faster time to results is the industry's greatest need to minimize risk and cost by providing better control of factory hygiene and food safety, and enabling quicker corrective actions. Furthermore, since inventory is often held until results are available, there is a large incentive for rapid testing to minimize hold times. The cost of food recalls due to potential bacterial contamination can easily reach into the tens of millions of dollars. Rapid identification of bacteria is also a critical capability needed to effectively respond to potential acts of bioterrorism or use of bioweapons during military conflicts.

Detection of extremely low levels of pathogenic bacteria is important for all of these applications. Trace levels of bacteria in food can multiply to dangerous levels during transit, display and storage, and "ready-to-eat" foods like lunchmeat are particularly vulnerable. *Listeria* is notorious for its ability to continue to multiply even at refrigerated temperatures. Early diagnosis of human infection is needed for effective patient treatment. The consequences of delayed diagnosis can lead to serious health problems or even death. The ability to detect trace levels of bacteria in environmental samples or from air samples will allow identification and accurate geographical delineation of bioagent releases in the event of a terrorist attack or during military operations.

There are currently no means to detect trace levels of bacteria using even the most sensitive molecular approaches, such as polymerase chain reaction (PCR). The need to detect low levels of bacteria requires that an enrichment step be performed to grow the bacteria to a level that is detectable by current instrumentation. Thus, a need exists for methods to rapidly enrich and detect microorganisms.

SUMMARY

Methods for rapidly amplifying and detecting microorganisms, such as pathogenic microorganisms, are provided herein. The disclosed methods utilize gene-matched enrichment media and PCR-based detection.

Provided herein is a method for enrichment and detection of a microorganism. In some embodiments, the method includes amplifying the microorganism in partially spent enrichment media (which optionally includes chemical additives), wherein the spent enrichment media is produced by inoculating a suitable growth media with a modified microorganism, wherein the modified microorganism includes a plurality of silent mutations in at least one target gene (such as a virulence gene), allowing the modified microorganism to grow in the media for a selected period of time, and filtering the media to remove cells of the modified microorganism; isolating nucleic acid from the amplified microorganism; and detecting the presence of the microorganism by performing a PCR assay on the isolated nucleic acid using a pair of primers that hybridize with and amplify the target gene of the microorganism, but will not amplify the target gene from the modified microorganism. In some embodiments, the microorganism is *Listeria*. In some embodiments, the modified microorganism is of the same genus as the microorganism to be enriched and detected.

Further provided is a method of producing spent enrichment media. In some examples the method includes inoculating a suitable growth media with a modified microorganism that has a plurality of silent mutations in at least one target gene (such as a virulence gene); allowing the modified microorganism to grow in the media for a selected period of time; and filtering the media to remove cells of the modified microorganism. Spent enrichment media generated using the disclosed method is also provided.

Also provided are kits for detecting a microorganism. Such kits can include spent enrichment media produced according to the methods disclosed herein, and a set of oligonucleotide primers that permit amplification of the at least one target gene that does not have the plurality of silent mutations and/or a probe. In some embodiments, the spent enrichment media is lyophilized. In some embodiments, the microorganism is *Listeria*.

Modified *Listeria monocytogenes* that have a plurality of silent mutations in at least one target gene (such as a virulence gene) are further provided herein. Also provided is a method of making enrichment media for growth of *Listeria* species. In some embodiments, the method includes inoculating a suitable growth media with a bacterial culture comprising the modified *L. monocytogenes* having a plurality of mutations in at least one target gene; allowing growth of the bacterial culture in the media for a period of time sufficient to achieve an $OD_{600}$ of about 0.3 to about 0.5; and filtering the media to remove bacterial cells, thereby generating an enrichment media for growth of *Listeria* species.

Enrichment media for growth of *Listeria* generated according to the disclosed method is also provided by the present disclosure.

Further provided herein are primers and probes for amplification and detection of *Listeria* species, as well as PCR-based detection methods using the disclosed primers and/or probes. Kits for amplification and detection of *Listeria* species are also provided herein.

The foregoing and other objects and features of the disclosure will become more apparent from the following detailed description, which proceeds with reference to the accompanying figures.

BRIEF DESCRIPTION OF THE DRAWINGS

FIG. 1 is a graph showing fold change of *Listeria monocytogenes* 15353 after seven hours of growth in 25 mL of tryptic soy broth (TSB), custom *Listeria* enrichment media (CLEM)-2 or CLEM-3. *L. monocytogenes* 15353 was inoculated at 47 colony forming units (CFU) per culture.

FIG. 2 is a pair of graphs showing results of a PCR assay to detect *Listeria* DNA in CLEM-2 (left) and CLEM-3 (right).

FIG. 3 is a graph showing fold change of *L. monocytogenes* 15353 after seven hours of growth in 25 mL of TSB, CLEM-3 or CLEM-3 with additives. *L. monocytogenes* 15353 was inoculated at 47 CFU per culture.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Sep. 7, 2018, 2.17 KB, which is incorporated by reference herein. In the accompanying sequence listing:

SEQ ID NO: 1 is the wild-type actA gene target nucleic acid sequence.

SEQ ID NO: 2 is the silent mutation actA target nucleic acid sequence.

SEQ ID NO: 3 is the nucleotide sequence of a forward primer for amplification of wild-type actA.

SEQ ID NO: 4 is the nucleotide sequence of a reverse primer for amplification of wild-type actA.

SEQ ID NO: 5 is the nucleotide sequence of an actA probe.

SEQ ID NO: 6 is the wild-type ssrB gene target nucleic acid sequence.

SEQ ID NO: 7 is the silent mutation ssrB target nucleic acid sequence.

SEQ ID NO: 8 is the nucleotide sequence of a forward primer for amplification of wild-type ssrB.

SEQ ID NO: 9 is the nucleotide sequence of a reverse primer for amplification of wild-type ssrB.

SEQ ID NO: 10 is the nucleotide sequence of an ssrB probe.

DETAILED DESCRIPTION

I. Abbreviations

CFU colony forming units
CLEM custom *Listeria* enrichment media
OD optical density
PCR polymerase chain reaction
TSB tryptic soy broth

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Brain-heart infusion (BHI) medium: A highly nutritious general-purpose growth medium for culturing fastidious and nonfastidious microorganisms, such as streptococci, pneumococci and meningococci. It is made by boiling cow or porcine hearts and brains, which releases soluble factors into the broth. BHI medium generally contains brain-heart infusion (from solids), peptic digest of animal tissue, pancreatic digest of casein, sodium chloride, glucose and disodium hydrogen phosphate.

Casamino acids: A mixture of amino acids and very small peptides obtained from acid hydrolysis of casein; contains all essential amino acids except tryptophan.

Detectable label: An agent capable of detection, for example by ELISA, spectrophotometry, flow cytometry, fluorometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Enrichment media: Culture media that favors the growth of a particular type of microorganism, or group of microorganisms, such as to allow for more rapid amplification of the microorganism.

Gram-positive bacteria: Bacteria that stain dark blue or violet during Gram staining, and have a thick peptidoglycan layer. Exemplary Gram-positive bacteria that can be used to produce a spent enrichment media (for example when they contain a plurality of silent mutations in at least one virulence gene) and that can be detected using the disclosed methods include but are not limited to:

| | |
|---|---|
| *Actinobacteria* | *Enterococcus* |
| *Actinomyces* | *Lactobacillales* |
| *Actinomyces israelii* | *Listeria* |
| *Bacillales* | *Nocardia* |
| *Bacillus* | *Nocardia asteroides* |
| *Clostridium* | *Nocardia brasiliensis* |
| *Clostridium acetobutylicum* | *Propionibacterium acnes* |
| *Clostridium aerotolerans* | *Rhodococcus equi* |
| *Clostridium argentinense* | *Sarcina* |
| *Clostridium baratii* | *Solobacterium moorei* |

| | |
|---|---|
| Clostridium beijerinckii | Staphylococcus |
| Clostridium bifermentans | Staphylococcus aureus |
| Clostridium botulinum | Staphylococcus capitis |
| Clostridium butyricum | Staphylococcus caprae |
| Clostridium cadaveris | Staphylococcus epidermidis |
| Clostridium cellulolyticum | Staphylococcus haemolyticus |
| Clostridium chauvoei | Staphylococcus hominis |
| Clostridium clostridioforme | Staphylococcus lugdunensis |
| Clostridium colicanis | Staphylococcus muscae |
| Clostridium difficile | Staphylococcus nepalensis |
| Clostridium estertheticum | Staphylococcus pettenkoferi |
| Clostridium fallax | Staphylococcus saprophyticus |
| Clostridium formicaceticum | Staphylococcus succinus |
| Clostridium histolyticum | Staphylococcus warneri |
| Clostridium innocuum | Staphylococcus xylosus |
| Clostridium kluyveri | Strangles |
| Clostridium ljungdahlii | Streptococcus |
| Clostridium novyi | Streptococcus agalactiae |
| Clostridium paraputrificum | Streptococcus anginosus |
| Clostridium perfringens | Streptococcus bovis |
| Clostridium phytofermentans | Streptococcus canis |
| Clostridium piliforme | Streptococcus iniae |
| Clostridium ragsdalei | Streptococcus lactArius |
| Clostridium ramosum | Streptococcus mitis |
| Clostridium septicum | Streptococcus mutans |
| Clostridium sordellii | Streptococcus oralis |
| Clostridium sporogenes | Streptococcus parasanguinis |
| Clostridium sticklandii | Streptococcus peroris |
| Clostridium tertium | Streptococcus pneumoniae |
| Clostridium tetani | Streptococcus pyogenes |
| Clostridium thermosaccharolyticum | Streptococcus ratti |
| Clostridium tyrobutyricum | Streptococcus salivarius |
| Corynebacterium | Streptococcus sanguinis |
| Corynebacterium bovis | Streptococcus sobrinus |
| Corynebacterium diphtheriae | Streptococcus suis |
| Corynebacterium granulosum | Streptococcus salivarius thermophilus |
| Corynebacterium jeikeium | Streptococcus uberis |
| Corynebacterium minutissimum | Streptococcus vestibularis |
| Corynebacterium renale | Streptococcus viridans |

Gram-negative bacteria: Bacteria that loose or do not retain dark blue or violet stain during Gram staining, but instead are colored by a counterstain, such as safranin, and appear pink or red. Gram-negative bacteria have a thin peptidoglycan layer between an inner cell wall and a bacterial outer membrane. Exemplary Gram-negative bacteria that can be used to produce a spent enrichment media (for example when they contain a plurality of silent mutations in at least one virulence gene) and that can be detected using the disclosed methods include but are not limited to:

| | |
|---|---|
| Acinetobacter baumannii | Fusobacterium necrophorum |
| Agrobacterium tumefaciens | Fusobacterium nucleatum |
| Anaerobiospirillum | Fusobacterium polymorphum |
| Bacteroides | Haemophilus haemolyticus |
| Bacteroides fragilis | Haemophilus influenzae |
| Bdellovibrio | Helicobacter |
| Brachyspira | Helicobacter pylori |
| Cardiobacterium hominis | Klebsiella pneumoniae |
| Coxiella burnetii | Legionella |
| Cyanobacteria | Legionella pneumophila |
| Cytophaga | Leptotrichia buccalis |
| Dialister | Megamonas |
| Enterobacter | Megasphaera |
| Enterobacter cloacae | Moraxella |
| Enterobacteriaceae | Moraxella bovis |
| Escherichia | Moraxella catarrhalis |
| Escherichia coli | Moraxella osloensis |
| Rickettsia rickettsii | Morganella morganii |
| Salmonella | Negativicutes |
| Salmonella enterica | Neisseria gonorrhoeae |
| Salmonella enterica | Neisseria meningitidis |
| Selenomonadales | Neisseria sicca |
| Serratia marcescens | Pectinatus |
| Shigella | Propionispora |
| Spirochaeta | Proteobacteria |
| Spirochaetaceae | Proteus mirabilis |
| Sporomusa | Proteus penneri |
| Stenotrophomonas | Pseudomonas |
| Streptococcus gordonii | Pseudomonas aeruginosa |
| Vampirococcus | |
| Verminephrobacter | |
| Vibrio cholerae | |
| Wolbachia | |
| Zymophilus | |

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Isolated: An "isolated" microorganism (such as a virus, bacterium, fungus, or protozoan) has been substantially separated or purified away from microorganisms of different types, strains, or species. Microorganisms can be isolated by a variety of techniques, including serial dilution and culturing.

An "isolated" biological component (such as a nucleic acid molecule, protein or organelle) has been substantially separated or purified away from other biological components in the cell of the organism in which the component naturally occurs, such as other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant expression in a host cell, as well as chemically synthesized nucleic acids or proteins, or fragments thereof.

*Listeria*: A genus of bacteria that are facultatively anaerobic, Gram-positive bacilli. The *Listeria* genus contains ten species—*L. fleischmannii, L. grayi, L. innocua, L. ivanovii, L. marthii, L. monocytogenes, L. rocourtiae, L. seeligeri, L. weihenstephanensis* and *L. welshimeri*. The primary human pathogen in this genus is *L. monocytogenes*. *Listeria* can be found in soil (which can lead to vegetable contamination), uncooked meats, uncooked vegetables, fruit, pasteurized or unpasteurized milk, foods made from milk and processed foods.

*Listeria monocytogenes*: A food-borne pathogen that causes listeriosis. Listeriosis: A bacterial infection, most commonly caused by *L. monocytogenes*. Listeriosis primarily involves infections of the central nervous system (e.g., meningitis, meningoencephalitis, brain abscess, cerebritis etc.) and bacteremia in individuals that are immunocompromised, pregnant women, newborns and the elderly. *Listeria* is ubiquitous in the environment and is primarily transmitted via the oral route after ingestion of contaminated food products, after which the organism penetrates the intestinal tract to cause systemic infections. The diagnosis of listeriosis requires the isolation of the organism from the blood and/or the cerebrospinal fluid. Treatment currently includes prolonged administration of antibiotics, primarily ampicillin and gentamicin, to which the organism is usually susceptible.

Luria-Bertani medium: A widely used growth medium for bacteria. Luria-Bertani medium generally contains peptone or tryptone, yeast extract and sodium chloride.

Lyophilized media: Media that has been freeze-dried, such as to enable extended storage.

Microorganism: A microscopic organism that can be a single cell or multicellular organism. Examples of microorganisms include bacteria, viruses, fungi, nematodes, and protozoa. At least some microorganisms are pathogenic.

Modified microorganism: A microorganism that has been genetically altered to contain at least one mutation or to contain heterologous nucleic acid, such as two or more silent mutations in at least one gene, such as a virulence gene.

Nutrient broth: A liquid growth medium used for culturing bacteria. In the context of the present disclosure, "nutrient broth" contains beef extract and peptone.

Oligonucleotide: A polynucleotide sequence of up to about 300 nucleotide bases in length. In some embodiments, the oligonucleotide is about 5 to about 200 nucleotides in length. In particular embodiments, the oligonucleotide is about 10 to about 100 nucleotides in length, or about 15 to about 50 nucleotides in length. In specific examples, the oligonucleotide is about 18 to about 28 nucleotides in length, such as 18, 19, 20, 21, 22, 23, 24, 25, 26, 27 or 28 nucleotides in length.

Pathogen: An organism, such as a bacterial, viral, fungal or protozoan organism, capable of causing disease.

Peptone: An enzymatic digest of animal protein.

Peptone buffered water: A growth medium used for culturing bacteria. Peptone buffered water is often used to aid in the recovery of *Salmonella* species from food and other types of samples prior to enrichment and/or isolation. Peptone buffered water generally contains peptone, sodium chloride, disodium phosphate and monopotassium phosphate. This type of media is also known as "buffered peptone water."

Plurality: As used herein, "plurality" means at least two.

Primers and probes: Short nucleic acid molecules, for example oligonucleotides ten nucleotides or more in length. Primers are annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. Probes are used to detect a specific nucleic acid sequence by hybridization. In some embodiments, the primers or probes are at least 10, at least 12, at least 14, at least 16, at least 18, at least 20, at least 22, at least 24, at least 26, at least 28, at least 30, at least 32, at least 34, at least 36, at least 38 or at least 40 nucleotides in length.

When referring to a probe or primer, the term "specific for (a target sequence)" indicates that the probe or primer hybridizes under stringent conditions substantially only to the target sequence in a given sample comprising the target sequence.

Silent mutation: A nucleotide mutation that does not result in a change in amino acid sequence of the encoded protein.

Spent enrichment media: Enrichment media in which a microorganism has been previously cultured. In the context of the present disclosure, spent enrichment media is generated by inoculating a selected culture media with a microorganism (such as a microorganism containing a plurality of silent mutations in at least one target gene), allowing the microorganism to grow for a particular period of time and removing cells of the microorganism by filtration.

Target gene: In the context of the present disclosure, a "target gene" is a gene that is mutated in a modified microorganism (used for producing partially spent enrichment media). The PCR assay disclosed herein is designed to amplify the corresponding target gene in the organism to be identified. In some embodiments, the target gene is a virulence gene. In other examples, the target gene is a gene specific for a particular genus.

Tryptic soy broth (TSB): A general purpose culture medium for growth of a wide variety of microorganisms. TSB generally contains peptone (such as casein peptone and/or soy peptone), dipotassium hydrogen phosphate (or disodium hydrogen phosphate), glucose and sodium chloride. TSB, also known as soybean-casein digest medium, is available commercially from a variety of sources. TSB may or may not contain dextrose.

Virulence gene: A gene whose presence or activity in a microorganism's genome contributes to the pathogenicity of the microorganism. For example, a virulence gene may enable the microorganism to establish itself on or within a host of a particular species and/or enhance its potential to cause disease. Virulence genes of bacteria encode, for example, bacterial toxins, cell surface proteins that mediate bacterial attachment, cell surface carbohydrates and proteins that protect a bacterium, and hydrolytic enzymes that contribute to pathogenicity of a bacterium.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Methods for rapidly amplifying and detecting microorganisms, such as pathogenic microorganisms, are provided herein. The disclosed methods utilize gene-matched enrichment media and PCR-based detection. The enrichment media is partially spent media produced using a modified microorganism containing a plurality of mutations in a selected gene such that the modified microorganism does not contain the PCR signature. Thus, PCR detects only the amplified microorganism of interest, not the modified microorganism used to generate the enrichment media. This complementary, gene-matched enrichment and PCR-based method enables the use of spent media without generating false-positive PCR results.

The methods, kits and compositions disclosed herein can be used to amplify and detect any type of microorganism, including bacteria, fungi, protozoa and nematodes. Furthermore, the disclosed methods, kits and compositions are broadly applicable to a number of different fields, including food safety, clinical diagnostics, homeland security and defense (e.g., for the detection of biological weapons). The present disclosure is particularly suited to applications in which amplification and detection of very low levels of a microorganism in a given sample are required, and/or for detection of slow growing microorganisms. For example, the methods, kits and compositions disclosed herein can be used to detect about 1 to about 1000 CFU of a microorganism per sample, such as about 1 to about 500 CFU/sample, about 1 to about 250 CFU/sample, about 1 to about 100 CFU/sample, about 1 to about 50 CFU/sample, about 1 to about 25 CFU/sample or about 1 to about 10 CFU/sample.

Specific methods, kits and compositions for rapid amplification and detection of *Listeria* species are also described, but one skilled in the art will appreciate that based on the teachings provided herein, other microorganisms of interest can be used instead of *Listeria*.

A. Gene-Matched Enrichment and Detection Methods

Provided herein are methods for enrichment and detection of a microorganism. In some embodiments, the method includes amplifying the microorganism in spent enrichment media, wherein the spent enrichment media is produced by inoculating a suitable growth media with a modified microorganism, wherein the modified microorganism includes a plurality of silent mutations in at least one target gene (such as a virulence gene), allowing the modified microorganism to grow in the media for a selected period of time, and filtering the media to remove cells of the modified microorganism; isolating nucleic acid from the amplified microorganism; and detecting the presence of the microorganism in the sample by performing a PCR assay on the isolated nucleic acid using a pair of primers that hybridize with and amplify the target gene of the microorganism, but will not amplify the target gene from the modified microorganism. In some embodiments, the modified microorganism is of the same genus as the microorganism to be detected. In other embodiments, the microorganism is of the same type (i.e. viral, bacterial, fungal, nematode), but not of the same genus. For example, the modified microorganism may be selected based on particular properties, such as the ability to enhance the growth of the microorganism to be detected (particularly a slow growing microorganism), but inhibiting the growth of fast growing microorganisms. As one example, for enrichment and detection of *E. coli* or *Salmonella*, a modified *Listeria* species could be used to generate the enrichment media. One of skill in the art is capable of selecting an appropriate microorganism to prepare the enrichment media.

In some embodiments, the plurality of mutations is 2 to 100, 2 to 50, 2 to 20, or 2 to 12, such as 2, 3, 4, 5, 6, 7, 8, 9, 10, 11 or 12 mutations.

A suitable growth media can be selected by one of skill in the art depending upon, for example, the type of microorganism that is suspected of being present in a sample to be tested. In some embodiments, the growth media is TSB without dextrose, TSB with dextrose, brain-heart infusion (BHI) media, Luria-Bertani media, nutrient broth or peptone buffered water. The growth media optionally includes additional components such as, but not limited to, blood (bovine or sheep), beef extract, M9 salts or casamino acids. The modified microorganism is allowed to grow in the media for a period of time, such as a period of time sufficient to reach a desired optical density (OD). In some embodiments, the modified microorganism is allowed to grow in the media until reaching an $OD_{600}$ of about 0.3 to about 0.5, such as about 0.35 to about 0.45. In some embodiments, the microorganism is allowed to grow in the media for a specified period of time, such as about 1 hour to about 8 hours, such as about 1, 2, 3, 4, 5, 6, 7 or 8 hours.

After growth for a sufficient or selected period of time, cells of the modified microorganism are filtered from the enrichment media using standard procedures. In some embodiments, the pore size of the filter is about 0.20 to about 0.25 μm, such as about 0.22 μm. Filtration removes cells of the modified microorganism from the media, but may not remove cellular debris and/or nucleic acid of the modified microorganism. However, the residual nucleic acid is derived from the modified microorganism having a plurality of silent mutations in at least one target gene. Thus, any nucleic acid in the spent media does not contain the PCR signature (i.e., does not contain a wild-type version of the target gene and will not be amplified using the gene-matched PCR assay).

Once the spent media is filtered, it can be used for amplification of a microorganism from a sample, such as, but not limited to, a sample obtained from a subject suspected of being infected with a microorganism; a food or drink sample suspected of being contaminated with a microorganism; a water, air, or soil sample suspected of containing a microorganism; or a sample obtained from wiping a surface suspected of harboring a microorganism.

In some embodiments, the microorganism is amplified in the spent enrichment media for a period of time sufficient to enable isolation of nucleic acid from the microorganism. In some examples, the microorganism is amplified in the spent enrichment media until reaching an $OD_{600}$ of about 0.3 to about 0.5, such as about 0.35 to about 0.45. In some examples, the microorganism is amplified in the spent enrichment media for a specified period of time, such as about 1 hour to about 8 hours, such as about 1, 2, 3, 4, 5, 6, 7 or 8 hours. In other examples, a longer growth period is required for amplification of the microorganism, such as about 8 hours to about 24 hours.

Once amplified, nucleic acid from the microorganism is isolated according to standard procedures well-known in the art. PCR is performed to amplify the isolated nucleic acid using primers that will hybridize to and amplify at least one of the target genes, but will not amplify nucleic acid from a modified microorganism including a plurality of silent mutations in the target gene.

In some cases, the target gene selected is specific for a genus of microorganism (i.e., it is present in all or a majority of the species of the genus), and will therefore detect any species of microorganism from that genus. In other instances, the target gene selected is specific for one species (or a small number of species) of the genus, and will thus allow for detection of only the particular species.

The microorganism to be amplified and detected can be any microorganism capable of being cultured in a growth medium. For example, the microorganism can be a bacterium, fungus, protozoan or nematode. Exemplary genera (and in some cases species) of bacteria, fungus, protozoa and nematodes are provided below in section IV.

In some embodiments, the microorganism is a bacterial microorganism. In particular embodiments, the genus of the bacterial microorganism is *Acetobacter, Acinetobacter, Actinomyces, Aerobacter, Agrobacterium, Alcaligenes, Anabaena, Arthrobacter, Bacillus, Bacteriodes, Bdellovibrio, Beggiatoa, Beijerinckia, Bifidobacterium, Bordetella, Borrelia, Brucella, Burkholderia, Campylobacter, Caulobacter, Chlamydia, Chlamydophila, Cholorobium, Chromatium, Citrobacter, Clostridium, Corynebacterium, Coxiella, Cryptobacterium, Cytophaga, Desulfovibrio, Diplococcus, Enterobacter, Enterococcus, Erwinia, Escherichia, Flexibacter, Francisella, Frankia, Gallionella, Haemophilus, Halobacterium, Heliobacter, Hydrogenomonas, Hyphomicrobium, Klebsiella, Lactobacillus, Legionella, Leptospira, Leptothrix, Leuconostoc, Listeria, Methanobacterium, Methylococcus, Methylomonas, Micrococcus, Mycobacterium, Mycoplasma, Neisseria, Nitrobacter, Nitrosomonas, Nocardia*, or *Pasteurella*.

In some examples, the genus of the bacteria is *Listeria, Bacillus, Bartonella, Bordetella, Brucella, Burkholderia, Campylobacter, Chlamydia, Clostridium, Corynebacterium, Enterococcus, Escherichia, Haemophilus, Helicobacter, Legionella, Mycobacterium, Mycoplasma, Neisseria, Pseudomonas, Salmonella, Shigella, Staphyloccocus, Streptococcus, Vibrio* or *Yersinia*.

In other examples, the genus of the bacteria is *Bacillus, Bordetella, Borrelia, Brucella, Burkholderia, Campylobacter, Chlamydia, Clostridium, Corynebacterium, Coxiella, Cryptobacterium, Enterobacter, Enterococcus, Escherichia, Francisella, Haemophilus, Heliobacter, Klebsiella, Legionella, Listeria, Mycobacterium, Mycoplasma*, or *Neisseria*.

In some examples, the bacterial microorganism is a species of *Listeria*. In some examples, the at least one target gene of *Listeria* is selected from inlA, inlB, plcA, hylA, actA, plcB, ssrB, ssrA and iap (RefSeq lmo0433, lmo0434, lmo0201, lmo0204, lmo0205, lmo2448, lmo2765 and lmo0582). In particular examples, the at least one target gene includes actA or ssrB, or both.

In other examples, the bacterial microorganism is *Bacillus cereus* and the target gene is hblC, hblD, hblA, nheA, nheB, nheC, entF, entM or eytK.

In other examples, the bacterial microorganism is *Escherichia coli* and the target gene is fedA, $stx_{2e}$, faeG, fanA, fasA, est or elt.

In yet other examples, the bacterial microorganism is *Clostridium perfringens* and the target gene is plc, pfoA, cola or nahH.

B. Spent Enrichment Media and Methods of Producing the Media

Methods for producing spent enrichment media are provided. The methods can include inoculating a suitable growth media with a modified microorganism having a plurality of silent mutations in at least one target gene (such as a virulence gene); allowing the modified microorganism to grow in the media for a selected period of time; and filtering the media to remove cells of the modified microorganism.

In some embodiments, the plurality of mutations is 2 to 100, 2 to 50, 2 to 20, or 2 to 12, such as 2, 3, 4, 5, 6, 7, 8, 9, 10, 11 or 12 mutations.

A suitable growth media can be selected by one of skill in the art depending upon, for example, the type of modified microorganism that will be used to generated the spent media, and the type of microorganism that is suspected of being present in a sample to be tested. In some embodiments, the growth media is TSB without dextrose, TSB with dextrose, brain-heart infusion (BHI) media, Luria-Bertani media, nutrient broth or peptone buffered water. The growth media optionally includes additional components such as, but not limited to, blood (bovine or sheep), beef extract, M9 salts or casamino acids. The modified microorganism is allowed to grow in the media for a period of time, such as a period of time sufficient to reach a desired OD. In some embodiments, the modified microorganism is allowed to grow in the media until reaching an $OD_{600}$ of about 0.3 to about 0.5, such as about 0.35 to about 0.45. In some embodiments, the microorganism is allowed to grow in the media for a specified period of time, such as about 1 hour to about 8 hours, such as about 1, 2, 3, 4, 5, 6, 7 or 8 hours.

After growth for a sufficient or selected period of time, cells of the modified microorganism are filtered from the enrichment media using standard procedures. In some embodiments, the pore size of the filter is about 0.20 to about 0.25 μm, such as about 0.22 μm.

In some embodiments, the method further includes lyophilizing the spent enrichment media.

Spent enrichment media (including lyophilized spent enrichment media) generated using the methods disclosed herein is also provided. As noted above, filtration of the enrichment media following growth of the modified microorganism removes cells of the modified microorganism from the media, but may not remove cellular debris and/or nucleic acid of the modified microorganism. However, the residual nucleic acid is derived from the modified microorganism having a plurality of silent mutations in at least one target gene. Thus, any nucleic acid in the spent enrichment media does not contain the PCR signature (i.e. does not contain a wild-type version of the target gene and will not be amplified using the gene-matched PCR assay).

The spent enrichment media optionally further includes one or more additives to enhance growth of the microorganism. For example, the spend enrichment media may further include L-glutamine, biotin, Tween-20, glucose, KC1, norepinephrine and/or L-alanine.

Further provided are lyophilized preparations of the spent enrichment media disclosed herein.

Also provided herein is a method of making enrichment media for growth of *Listeria* species. In some embodiments, the method includes inoculating a suitable growth media with a bacterial culture including a modified *L. monocytogenes* having a plurality of mutations in at least one target gene (such as a virulence gene); allowing growth of the bacterial culture in the media for a selected period of time; and filtering the media to remove bacterial cells.

A media suitable for growth of *Listeria* can be selected by one of skill in the art. In some embodiments, the suitable growth media is tryptic soy broth (TSB), such as TSB without dextrose, or TSB with dextrose. The modified *L. monocytogenes* is allowed to grow in the media for a period of time, such as a period of time sufficient to reach a desired OD. In some embodiments, the modified *L. monocytogenes* is allowed to grow in the media until reaching an $OD_{600}$ of about 0.3 to about 0.5, such as about 0.35 to about 0.45. In some embodiments, the modified *L. monocytogenes* is allowed to grow in the media for a specified period of time, such as about 1 hour to about 8 hours, such as about 1, 2, 3, 4, 5, 6, 7 or 8 hours.

After growth for a sufficient or selected period of time, cells of the modified *L. monocytogenes* are filtered from the enrichment media using standard procedures. In some embodiments, the pore size of the filter is about 0.20 to about 0.25 μm, such as about 0.22 μm. Filtration removes bacterial cells from the media, but may not remove cellular debris and/or nucleic acid of the modified *L. monocytogenes*.

In some embodiments, the method further includes lyophilizing the spent enrichment media.

Enrichment media (including lyophilized enrichment media) for growth of *Listeria* generated according to the disclosed methods is also provided by the present disclosure.

In some embodiments, the enrichment media for growth of *Listeria* includes modified *L. monocytogenes* nucleic acid having the nucleotide sequence of SEQ ID NO: 2 or SEQ ID NO: 7 (or a fragment thereof having at least one silent mutation relative to the wild-type sequence such that it is not amplified by the gene-matched PCR assay).

In some embodiments, the enrichment media further includes one or more additives. In some examples, the additives include L-glutamine, biotin, Tween-20, glucose, KCl, norepinephrine and/or L-alanine.

Also provided is a lyophilized preparation of the *Listeria* enrichment media.

C. Kits for Amplification and Detection of Microorganisms

Kits for detecting a microorganism are further provided by the present disclosure. In some embodiments, the kits include spent enrichment media produced according to the methods disclosed herein, and a pair of oligonucleotide primers that permit amplification of the at least one target gene that does not have the plurality of silent mutations.

In some embodiments, the spent enrichment media in the kit is lyophilized.

In some embodiments, the kit further includes a Taq DNA polymerase, deoxynucleotides (dNTPs), buffer, or any combination thereof.

The microorganism to be detected using the kit can be any type of bacterium, fungus, protozoan or nematode. Exemplary genera (and in some cases species) of bacteria, fungus, protozoa and nematodes are provided below in section IV.

In some embodiments, the microorganism is a bacterial microorganism. In particular embodiments, the genus of the bacterial microorganism is *Acetobacter, Acinetobacter, Actinomyces, Aerobacter, Agrobacterium, Alcaligenes, Anabaena, Arthrobacter, Bacillus, Bacteriodes, Bdellovibrio, Beggiatoa, Beijerinckia, Bifidobacterium, Bordetella, Borrelia, Brucella, Burkholderia, Campylobacter, Caulobacter, Chlamydia, Chlamydophila, Cholorobium, Chromatium, Citrobacter, Clostridium, Corynebacterium, Coxiella, Cryptobacterium, Cytophaga, Desulfovibrio, Diplococcus, Enterobacter, Enterococcus, Erwinia, Escherichia, Flexibacter, Francisella, Frankia, Gallionella, Haemophilus, Halobacterium, Heliobacter, Hydrogenomonas, Hyphomicrobium, Klebsiella, Lactobacillus, Legionella, Leptospira, Leptothrix, Leuconostoc, Listeria, Methanobacterium, Methylococcus, Methylomonas, Micrococcus, Mycobacterium, Mycoplasma, Neisseria, Nitrobacter, Nitrosomonas, Nocardia*, or *Pasteurella*.

In some examples, the genus of the bacteria is *Listeria, Bacillus, Bartonella, Bordetella, Brucella, Burkholderia, Campylobacter, Chlamydia, Clostridium, Corynebacterium, Enterococcus, Escherichia, Haemophilus, Helicobacter, Legionella, Mycobacterium, Mycoplasma, Neisseria, Pseudomonas, Salmonella, Shigella, Staphyloccocus, Streptococcus, Vibrio* or *Yersinia*.

In other examples, the genus of the bacteria is *Bacillus, Bordetella, Borrelia, Brucella, Burkholderia, Campylobacter, Chlamydia, Clostridium, Corynebacterium, Coxiella, Cryptobacterium, Enterobacter, Enterococcus, Escherichia, Francisella, Haemophilus, Heliobacter, Klebsiella, Legionella, Listeria, Mycobacterium, Mycoplasma*, or *Neisseria*.

In some examples, the microorganism is *Listeria*. In particular examples, the microorganism is *L. monocytogenes*.

In some examples in which the microorganism is *Listeria*, the at least one target gene is selected from inlA, inlB, plcA, hylA, actA, plcB, ssrB, ssrA and iap. In particular examples, the at least one target gene includes actA or ssrB, or both.

In other examples, the bacterial microorganism is *Bacillus cereus* and the target gene is hblC, hblD, hblA, nheA, nheB, nheC, entF, entM or eytK.

In other examples, the bacterial microorganism is *Escherichia coli* and the target gene is fedA, $stx_{2e}$, faeG, fanA, fasA, est or elt.

In yet other examples, the bacterial microorganism is *Clostridium perfringens* and the target gene is plc, pfoA, cola or nahH.

D. Modified *Listeria* monocytogenes

Modified *Listeria monocytogenes* bacteria having a plurality of silent mutations in at least one target gene (such as a virulence gene) are provided herein. In some embodiments, the at least one target gene is selected from inlA, inlB, plcA, hylA, actA, plcB, ssrB, ssrA and iap. In some examples, to enable genus-specific identification of *Listeria*, the at least one target gene is ssrB, ssrA and/or iap. In some examples, to enable species-specific detection of *L. monocytogenes*, the at least one target gene is inlA, inlB, plcA, hylA, actA, and/or plcB.

In some embodiments, the plurality of mutations is 2 to 100, 2 to 50, 2 to 20, or 2 to 12, such as 2, 3, 4, 5, 6, 7, 8, 9, 10, 11 or 12 mutations.

In some examples, the modified *L. monocytogenes* bacterium includes a plurality of mutations in the actA gene. In particular non-limiting examples, the modified *L. monocytogenes* has four silent mutations in the actA gene. In one example, the actA gene of the modified *L. monocytogenes* comprises SEQ ID NO: 2.

In some examples, the modified *L. monocytogenes* bacterium includes a plurality of mutations in the ssrB gene. In particular examples, the modified *L. monocytogenes* has seven silent mutations in the ssrB gene. In one example, the ssrB gene of the modified *L. monocytogenes* comprises SEQ ID NO: 7.

In some examples, the modified *L. monocytogenes* bacterium has a plurality of mutations in the actA gene and a plurality of mutations in the ssrB gene. In specific examples, the modified *L. monocytogenes* has four silent mutations in the actA gene and seven silent mutations in the ssrB gene. In particular examples, the actA gene includes SEQ ID NO: 2 and the ssrB gene includes SEQ ID NO: 7.

The modified *L. monocytogenes* disclosed herein can be used to produce spent enrichment media according to the methods disclosed herein (see section IIIB above).

E. Primers, Probes and Kits for Detection of *Listeria*

Further provided herein are primers and probes for amplification and detection of *Listeria* species, as well as PCR-based detection methods using the disclosed primers and/or probes. Kits for amplification and detection of *Listeria* species are also provided herein.

Provided are isolated nucleic acid molecules that are no more than about 50, no more than about 40, no more than about 30 or no more than about 25 nucleotides in length (such as 6 to 50, 6 to 40, 6 to 30, 6 to 25, 10 to 30, 10 to 25 or 12 to 25 nucleotides), including the nucleotide sequence of SEQ ID NO: 3, SEQ ID NO: 4, SEQ ID NO: 5, SEQ ID NO: 8, SEQ ID NO: 9 or SEQ ID NO: 10.

In some embodiments, the isolated nucleic acid molecule comprises a detectable label. In some examples, the detectable label comprises a fluorophore, a radioactive isotope, a chemiluminescent agent, an enzyme, a hapten or biotin. In some examples, the label is non-naturally occurring and/or does not occur naturally in combination with the isolated nucleic acid molecule.

Further provided are a pair of oligonucleotide primers, the sequences of which comprise SEQ ID NO: 3 and SEQ ID NO: 4; or SEQ ID NO: 8 and SEQ ID NO: 9. In some embodiments, at least one of the oligonucleotide primers includes a detectable label, such as, but not limited to a fluorophore, a radioactive isotope, a chemiluminescent agent, an enzyme, a hapten or biotin.

Also provided is a method for detecting a *Listeria* species in a sample. In some embodiments, the method includes amplifying nucleic acid in the sample by polymerase chain reaction using a pair of primers, wherein the pair of primers include the nucleotide sequences of SEQ ID NO: 3 and SEQ ID NO: 4; or SEQ ID NO: 8 and SEQ ID NO: 9, and detecting the amplified nucleic acid.

In some embodiments, detecting the amplified nucleic acid includes hybridizing the amplified nucleic acid with an oligonucleotide probe comprising SEQ ID NO: 5 or SEQ ID NO: 10.

In some embodiments, the *Listeria* species is *L. monocytogenes* or *L. ivanovii*

Further provided is a kit for detection of *Listeria* species. In some embodiments, the kit includes spent enrichment media for growth of *Listeria* as disclosed herein; and a pair of oligonucleotide primers, wherein at least one of the oligonucleotide primers includes the nucleotide sequence of SEQ ID NO: 3, SEQ ID NO: 4, SEQ ID NO: 8 or SEQ ID NO: 9.

In some examples, the enrichment media is lyophilized.

In some examples, the pair of oligonucleotide primers includes the sequences of SEQ ID NO: 3 and SEQ ID NO: 4; or SEQ ID NO: 8 and SEQ ID NO: 9.

In some examples, the kit further includes an oligonucleotide probe comprising the sequence of SEQ ID NO: 5 or SEQ ID NO: 10.

In specific examples, the pair of oligonucleotide primers includes the sequences of SEQ ID NO: 3 and SEQ ID NO: 4, and the oligonucleotide probe comprises the sequence of SEQ ID NO: 5.

In other specific examples, the pair of oligonucleotide primers includes the sequences of SEQ ID NO: 8 and SEQ ID NO: 9, and the oligonucleotide probe comprises the sequence of SEQ ID NO: 10.

In some embodiments, the kit further includes a Taq DNA polymerase, deoxynucleotides (dNTPs), buffer, or any combination thereof.

IV. Microorganisms

The methods, enrichment media and kits provided herein can be used to amplify and detect the presence of any one of a number of different microorganisms, such as pathogenic microorganisms. The microorganisms to be amplified and detected can be, for example, in a sample obtained from a subject, or found in food or the environment. In addition, microorganisms listed below, which have a plurality of silent mutations in at least one target gene, can be used to generate enrichment media. Exemplary microorganisms include, but are not limited to, bacteria, fungi, nematodes, and protozoa. A non-limiting list of microorganisms that can be amplified and detected using compositions and methods disclosed herein are provided below.

In some embodiments, the microorganism is a type of bacteria. Bacteria can generally be classified as gram-negative or gram-positive. Lists of gram-positive and gram-negative bacteria are provided above in "Terms and Methods." In some embodiments, the bacterium is selected from a genus or species listed below:

| | |
|---|---|
| *Acinetobacter baumannii* | *Megasphaera* |
| *Actinobacteria* | *Moraxella* |
| *Actinomyces* | *Moraxella bovis* |
| *Actinomyces israelii* | *Moraxella catarrhalis* |
| *Agrobacterium tumefaciens* | *Moraxella osloensis* |
| *Anaerobiospirillum* | *Morganella morganii* |
| *Bacillales* | *Negativicutes* |
| *Bacillus* | *Neisseria gonorrhoeae* |
| *Bacteroides* | *Neisseria meningitidis* |
| *Bacteroides fragilis* | *Neisseria sicca* |
| *Bdellovibrio* | *Nocardia* |
| *Brachyspira* | *Nocardia asteroids* |
| *Cardiobacterium hominis* | *Nocardia brasiliensis* |

| | |
|---|---|
| Clostridium | Pectinatus |
| Clostridium acetobutylicum | Propionibacterium acnes |
| Clostridium aerotolerans | Propionispora |
| Clostridium argentinense | Proteobacteria |
| Clostridium baratii | Proteus mirabilis |
| Clostridium beuerinckii | Proteus penneri |
| Clostridium bifermentans | Pseudomonas |
| Clostridium botulinum | Pseudomonas aeruginosa |
| Clostridium butyricum | Rhodococcus equi |
| Clostridium cadaveris | Rickettsia rickettsii |
| Clostridium cellulolyticum | Salmonella |
| Clostridium chauvoei | Salmonella enterica |
| Clostridium clostridioforme | Salmonella enterica enterica |
| Clostridium colicanis | Sarcina |
| Clostridium difficile | Selenomonadales |
| Clostridium estertheticum | Serratia marcescens |
| Clostridium fallax | Shigella |
| Clostridium formicaceticum | Solobacterium moorei |
| Clostridium histolyticum | Spirochaeta |
| Clostridium innocuum | Spirochaetaceae |
| Clostridium kluyveri | Sporomusa |
| Clostridium ljungdahlii | Staphylococcus |
| Clostridium novyi | Staphylococcus aureus |
| Clostridium paraputrificum | Staphylococcus capitis |
| Clostridium perfringens | Staphylococcus caprae |
| Clostridium phytofermentans | Staphylococcus epidermidis |
| Clostridium piliforme | Staphylococcus haemolyticus |
| Clostridium ragsdalei | Staphylococcus hominis |
| Clostridium ramosum | Staphylococcus lugdunensis |
| Clostridium septicum | Staphylococcus muscae |
| Clostridium sordellii | Staphylococcus nepalensis |
| Clostridium sporogenes | Staphylococcus pettenkoferi |
| Clostridium sticklandii | Staphylococcus saprophyticus |
| Clostridium tertium | Staphylococcus succinus |
| Clostridium tetani | Staphylococcus warneri |
| Clostridium thermosaccharolyticum | Staphylococcus xylosus |
| Clostridium tyrobutyricum | Stenotrophomonas |
| Corynebacterium | Strangles |
| Corynebacterium bovis | Streptococcus |
| Corynebacterium diphtheriae | Streptococcus agalactiae |
| Corynebacterium granulosum | Streptococcus anginosus |
| Corynebacterium jeikeium | Streptococcus bovis |
| Corynebacterium minutissimum | Streptococcus canis |
| Corynebacterium renale | Streptococcus gordonii |
| Coxiella burnetii | Streptococcus iniae |
| Cyanobacteria | Streptococcus lactArius |
| Cytophaga | Streptococcus mitis |
| Dialister | Streptococcus mutans |
| Enterobacter | Streptococcus oralis |
| Enterobacter cloacae | Streptococcus parasanguinis |
| Enterobacteriaceae | Streptococcus peroris |
| Enterococcus | Streptococcus pneumoniae |
| Escherichia | Streptococcus pyogenes |
| Escherichia coli (e.g., K-12 or O157:H7) | Streptococcus ratti |
| Fusobacterium necrophorum | Streptococcus salivarius |
| Fusobacterium nucleatum | Streptococcus salivarius thermophilus |
| Fusobacterium polymorphum | Streptococcus sanguinis |
| Haemophilus haemolyticus | Streptococcus sobrinus |
| Haemophilus influenzae | Streptococcus suis |
| Helicobacter | Streptococcus uberis |
| Helicobacter pylori | Streptococcus vestibularis |
| Klebsiella pneumoniae | Streptococcus viridans |
| Lactobacillales | Vampirococcus |
| Legionella | Verminephrobacter |
| Legionella pneumophilia | Vibrio cholerae |
| Leptotrichia buccalis | Wolbachia |
| Listeria | Zymophilus |
| Megamonas | |

Protozoa, nematodes, and fungi are also types of microorganisms.

Exemplary protozoa include, but are not limited to, Plasmodium (e.g., Plasmodium falciparum), Leishmania, Acanthamoeba, Giardia, Entamoeba (such as E. histolytica), Cryptosporidium, Isospora, Balantidium, Trichomonas, Trypanosoma (e.g., Trypanosoma brucei, Trypanosoma cruzi), Naegleria fowleri, and Toxoplasma (e.g. Toxoplasma gondii).

Exemplary fungi include, but are not limited to, Candida species (such as C. albicans), Aspergillus species (such as A. fumigatus and A. flavus), Cryptococcus species (such as C. neoformans and C. gattii), Histoplasma capsulatum, Pneumocystis jirovecii, Stachybotrys chartarum, Exserohilum rostratum, Mucoromycotina fungi, Cladosporium species, Sporothrix schenckii, Coccidiodes immitis and Blastomyces dermatitidis.

Exemplary nematodes include, but are not limited to, ascarids (Ascaris, e.g. A. lumbricoides), filarias, hookworms, pinworms (Enterobius), whipworms (Trichuris trichiura), Baylisascaris, Dirofilaria immitis and Haemonchus contortus.

V. Target Genes

The compositions and methods disclosed herein utilize modified microorganisms having silent mutations in at least one selected gene (referred to herein as the "target gene"). In some embodiments, the target gene is a virulence gene. Virulence genes from a wide variety of microorganisms are well known in the art and can readily be identified and selected using publically accessible sources.

Provided below are exemplary pathogenic bacteria genera (with exemplary species in parentheses), and a list of known target/virulence genes that can be mutated:

Listeria (L. monocytogenes, L. seeligeri, L. welshimeri, L. innocua, L. ivanovii, L. grayi)
  actA, agrA, agrC, ami, aut, bsh, cheA, cheY, dltA, fbpA, gtcA, hly, hpt, iap/cwhA, inlA, inlB, inlC, inlF, inlJ, inlK, lap, lapB, lgt, lisK, lisR, lntA, lpeA, lplA1, lspA, mpl, oatA, oppA, pdgA, plcA, plcB, prfA, prsA2, srtA, srtB, stp, svpA, vip, virR, virS Bacillus (B. anthracis, B. cereus, B. clausii, B. halodurans, B. licheniformis, B. subtilis, B. thuringiensis)
  atxA, capA, capB, capC, capD, capE, cry, cya, cyt, cytK, hblA, hblB, hblC, hblD, hlyII, hlyIII, inhA, lef, nheA, nheB, nheC, pagA, piplc, plcA, plcR, vip Bartonella (B. bacilliformis, B. quintana, B. henselae, B. tribocorum)
  atxA, capA, capB, capC, capD, capE, cry, cya, cyt, cytK, hblA, hblB, hblC, hblD, hlyII, hlyIII, inhA, lef, nheA, nheB, nheC, pagA, piplc, plcA, plcR, vip, atxA, capA, capB, capC, capD, capE, cry, cya, cyt, cytK, hblA, hblB, hblC, hblD, hlyII, hlyIII, inhA, lef, nheA, nheB, nheC, pagA, piplc, plcA, plcR, vip, atxA, capA, capB, capC, capD, capE, cry, cya, cyt, cytK, hblA, hblB, hblC, hblD, hlyII, hlyIII, inhA, lef, nheA, nheB, nheC, pagA, piplc, plcA, plcR, vip, atxA, capA, capB, capC, capD, capE, cry, cya, cyt, cytK, hblA, hblB, hblC, hblD, hlyII, hlyIII, inhA, lef, nheA, nheB, nheC, pagA, piplc, plcA, plcR, vip Bordetella (B. pertussis, B. parapertussis, B. bronchiseptica, B. avium, B. hinzii, B. holmesii, B. trematum, B. petri)
  bcr4, bcrD, bcrH1, bcrH2, bopB, bopC, bopD, bopN, bplA, bplB, bplC, bplD, bplE, bplF, bplG, bplH, bplI, bplJ, bplL, brkA, brkB, bscC, bscD, bscE, bscF, bscI, bscJ, bscK, bscL, bscN, bscO, bscP, bscQ, bscR, bscS, bscT, bscU, bscW, bsp22, btrS, bvgA, bvgS, cyaA, dnt, fhaB, fhaL, fha-like, fhaS, fim2, fim3, fimA, fimB, fimC, fimD, fimN, fimX, flaA, flaG, flgA, flgB, flgC, flgD, flgE, flgF, flgG, flgH, flgI, flgJ, flgK, flgL, flgM, flhA, flhB, flhC, flhD, flhF, fliA, fliD, fliE, fliF, fliG, fliH, fliI, fliJ, fliK, fliL, fliM, fliN, fliO, fliP, fliQ, fliR, fliS, fliT, motA, motB, pagP, prn, ptlA, ptlB, ptlC, ptlD, ptlE, ptlF, ptlG, ptlH, ptlI, ptxA, ptxB, ptxC, ptxD, ptxE, sphB 1, tcfA, wbmA, wbmB, wbmC, wbmD, wbmE, wbmF, wbmG, wbmH, wbmI, wbmJ, wbmK, wbmL, wbmM, wbmN, wbmO, wbmP, wbmQ, wbmR, wbmS, wbmT, wbmU

*Brucella* (*B. melitensis, B. abortus, B. suis, B. ovis* and *B. canis*)

acpXL, bvrR, bvrS, cgs, dhbA, dhbB, dhbC, dhbE, entD, fabZ, gmd, htrB, kdsA, kdsB, lpsA, lpsB/lpcC, lpxA, lpxB, lpxC, lpxD, lpxE, lpxK, manAoAg, manBcore, manCcore, manCoAg, per, pgm, pmm, vibH/entF, virB 1, virB 10, virB 11, virB2, virB3, virB4, virB5, virB6, virB7, virB8, virB9, waaA/kdtA, wbdA, wbkA, wbkB, wbkC, wboA, wbpL, wbpZ, wzm, wzt

*Burkholderia* (*B. pseudomallei, B. mallei, B. cenocepacia, B. thailandensis*)

bapA, bapB, bapC, basJ, bicA, bicP, bimA, bipB, bipC, bipD, boaA, boaB, bopA, bopC, bopE, bprA, bprB, bprC, bprD, bprP, bprQ, bsaK, bsaL, bsaM, bsaN, bsaO, bsaP, bsaQ, bsaR, bsaS, bsaT, bsaU, bsaV, bsaX, bsaY, bsaZ, bspI2, bspI3, bspR2, bspR3, bspR4, bspR5, cheA, cheB, cheD, cheR, cheW, cheY, cheY 1, cheZ, clpV, flgA, flgB, flgC, flgD, flgE, flgF, flgG, flgH, flgI, flgJ, flgK, flgL, flgM, flgN, flhA, flhB, flhF, flhG, fliA, fliG, fliD, fliE, fliF, fliG, fliH, fliI, fliJ, fliK, fliL, fliM, fliN, fliO, fliP, fliQ, fliR, fliS, gmhA, manC, motA, motB, orgA, orgB, pilA, pilB, pilC, pilD, pilN, pilO, pilQ, pilR, pilS, pilT, pilV, pmlI/bspII, pmlR/bspR1, spaP, tsr, wcbA, wcbB, wcbC, wcbD, wcbE, wcbF, wcbG, wcbH, wcbI, wcbJ, wcbK, wcbL, wcbM, wcbN, wcbO, wcbP, wcbQ, wcbR, wcbS, wcbT, wzm, wzt2

*Campylobacter* (*C. jejuni, C. coli, C. fetus*)

cadF, cdtA, cdtB, cdtC, ciaB, flaA, flaB, flaC, flaD, flaG, flgB, flgC, flgD, flgE, flgE2, flgG, flgG2, flgH, flgI, flgK, flgR, flhA, flhB, flhF, flhG, fliA, fliD, fliE, fliF, fliG, fliH, fliI, fliL, fliM, fliN, fliP, fliQ, fliR, fliS, fliY, jlpA, maf1, maf3, maf4, maf6, maf7, motA, motB, neuB2, neuC2, pebA, pglA, pglB, pglC, pglD, pglE, pglF, pglG, pglH, pglI, pglJ, plfA, porA, pseA, pseB, pseC, pseD, pseE, pseF, pseG, pseH, pseI, ptmA, ptmB, sapA, sapA-like, virB10, virB4, virB8, virB9, virD4

*Chlamydia* (*C. abortus, C. Caviae, C. felis, C. muridarum, C. pneumoniae, C. trachomatis*)

cdsC, cdsJ, cdsL, cdsN, cdsQ, cdsR, cdsS, cdsT, cdsU, cdsV, copB, copB2, copD, copN, incA, incB, incC, pkn5, sccl, ssc2, ssc3, tarp

*Clostridium* (*C. tetani, C. perfringens, C. botulinum, C. difficile, C. acetobutylicum, C. beijerinckii, C. phytofermentans, C. thermocellum, C. kluyveri, C. novyi*)

atx, cdtA, cdtB, cloSI, colA, cpb2, cpe, cwp66, entA, entB, entC, entD, fbp, groEL, nagH, nagI, nagJ, nagK, nagL, nanH, nanI, nanJ, pfoA, plc, slpA, tcnA, tetX, toxA, toxB, virR, virS

*Corynebacterium* (*C. diphtheria, C. jeikeium, C. efficiens, C. glutamicum, C. pseudotuberculosis*)

cbpA, ciuA, ciuB, ciuC, ciuD, ciuE, dtxR, fagA, fagB, fagC, fagD, hmuT, hmuU, hmuV, irp6A, irp6B, irp6C, pld, sapA, sapD, sapE, spaA, spaB, spaC, spaD, spaE, spaF, spaG, spaH, spaI, srtA, srtB, srtC, srtD, srtE, tox

*Enterococcus* (*E. faecalis, E. faecium, E. durans, E. avium, E. gallinarum, E. casseliflavus*)

ace, asa1, bopD, cpsA, cpsB, cpsC, cpsD, cpsE, cpsF, cpsG, cpsH, cpsI, cpsJ, cpsK, cylA, cylB, cylI, cylL-l, cylL-s, cylM, cylR1, cylR2, efaA, esp, fsrA, fsrB, fsrC, gelE, prgB/asc10, sprE

*Escherichia* (*E. coli*)

aafA, aafB, aafC, aafD, aaiA, aaiB, aaiC/hcp, aaiD, aaiE, aaiF, aaiH, aail, aaiJ, aaiK, aaiL, aaiM, aaiN, aap, aatA, aatA, aatB, aatC, aatD, aatP, aec11, aec14, aec15, aec16, aec17, aec18, aec19, aec22, aec23, aec24, aec25, aec26, aec27/clpV, aec28, aec29, aec30, aec31, aec32, aec7, aec8, agg3A, agg3B, agg3C, agg3D, aggR, agn43, aida, air/eaeX, astA, cah, cdiA, cdiB, cdtA, cdtB, cdtC, cesD, cesD2, cesF, cesT, cfaA, cfaB, cfaC, cfaD, chuA, chuS, chuT, chuU, chuW, chuX, chuY, cif, clpV/aaiP, cnfl, eae, eaeH, ecpA, ecpB, ecpC, ecpD, ecpE, ecpR, ehaA, ehaB, eltA, eltB, escC, escD, escF, escJ, escN, escR, escS, escT, escU, escV, espA, espB, espB, espC, espD, espF, espFu/tccP, espG, espG2, espH, espI, espJ, espK, espL1, espL2, espL4, espM1, espM2, espN, espO1-1, espO1-2, espP, espR1, espR3, espR4, espV, espW, espX1, espX2, espX4, espX5, espX6, espX7, espy 1, espY2, espY3, espY4, espY5, etpA, faeC, faeD, faeE, faeE, faeG, faeH, fael, faeJ, fimA, fimB, fimC, fimD, fimE, fimF, fimG, fimH, fimI, focA, focC, focD, focF, focG, focH, focI, fyuA, glrA, glrR, hlyA, hlyB, hlyC, hlyD, hlyE/clyA, ibeA, ibeB, ibeC, icmF/aaiO, ireA, iroB, iroC, iroD, iroE, iroN, irp1, irp2, iucA, iucB, iucC, iucD, iutA, ler, lifA/efal, map, nleA, nleB1, nleB2-1, nleB2-2, nleC, nleD, nleE-1, nleE-2, nleF, nleG-1, nleG-2, nleG2-2, nleG2-3, nleG2-4, nleG-3, nleG5-1, nleG5-2, nleG6-1, nleG6-2, nleG6-3, nleG7, nleG8-2, nleH1-1, nleH1-2, paa, papA, papB, papC, papD, papE, papF, papG, papH, papI, papJ, papK, papX, pet, pic, sat, senB, sepL, sepQ, sepZ, set1A, set1B, sfaA, sfaB, sfaC, sfaD, sfaE, sfaF, sfaG, sfaH, sfaS, sitA, sitB, sitC, sitD, stx1A, stx1B, stx2A, stx2B, tccP2, tia, tibA, tir, toxB, tsh, upaG/ehaG, upaH, usp, vat, vgrG, ybtA, ybtE, ybtP, ybtQ, ybtS, ybtT, ybtU, ybtX

*Haemophilus* (*H. influenzae, H. ducreyi, H. somnus*)

cdtA, cdtB, cdtC, comE/pilQ, flp1, flp2, flp3, flpB, flpC, flpD, galE, galE, galU, galU, gmhA/lpcA, hap, hemA, hemB, hemC, hemD, hemE, hemG, hemH, hemL, hemM, hemN, hemR, hemX, hemY, hgbA, hgpA, hgpB, hgpC, hgpD, hhdA, hhdB, hia/hsf, hifA, hifB, hifC, hifD, hifE, hitA, hitB, hitC, hmw1A, hmw1B, hmw1C, hmw2A, hmw2B, hmw2C, htrB, hxuA, hxuB, hxuC, iga1, kdkA, kdsA, kdsB, kdtA, kfiC, kpsF, lex2A, lex2B, lgtA, lgtC, lgtF, lic2A, lic3A, licA, licB, licC, licD, lpsA, lpt6, lpxA, lpxB, lpxC, lpxD, lpxH, lpxK, lsgA, lsgB, lsgC, lsgD, lsgE, lsgF, manA, manB, mrsA/glmM, msbA, msbB, neuA, oapA, ompP2, ompP5, opsX/rfaC, orfE, orfM, orfO, pgi, pilA, pilB, pilC, pilD, rcpA, rcpB, rfaD, rfaE, rfaF, rffG, siaA, tadA, tadB, tadC, tadD, tadE, tadF, tadG, tbpA, tbpB, waaQ, wbaP/rfbP, wecA, yhbX, yhxB/manB

*Helicobacter* (*H. pylori, H. hepaticus, H. acinonychis*)

alpA/hopC, alpB/hopB, babA/hopS, babB/hopT, cag1, cag2, cag3, cag4, cag5, cagA, cagC, cagD, cagE, cagF, cagG, cagH, cagI, cagL, cagM, cagN, cagP, cagQ, cagS, cagT, cagU, cagV, cagW, cagX, cagY, cagZ, cdtA, cdtB, cdtC, dupA, flaA, flaB, flaG, flaG, flgA, flgB, flgC, flgD, flgE_1, flgE_2, flgG_1, flgG_2, flgH, flgI, flgK, flgL, flhA, flhB_1, flhB$_{13}$ 2, flhF, fliA, fliD, fliE, fliF, fliG, fliH, fliI, fliL, fliM, fliN, fliP, fliQ, fliR, fliS, fliY, futA, futB, futC, hopZ, horB, hpaA, motA, motB, napA, oipA/hopH, peb1, pflA, sabA/hopP, sabB/hopO, ureA, ureB, ureE, ureF, ureG, ureH, ureI, vacA, virB11

*Legionella* (*L. pneumophilia*)

ccmA, ccmB, ccmC, ccmD, ccmE, ccmF, csrA, dotA, dotB, dotC, dotD, drrA/sidM, enhA, enhB, enhC, feoA, feoB, frgA, htpB, icmB/dotO, icmC/dotE, icmD/dotP, icmE/dotG, icmF, icmG/dotF, icmH/dotU, icmJ/dotN, icmK/dotH, icmL/dotI, icmM/dotJ, icmN/dotK, icmO/dotL, icmP/dotM, icmQ, icmR, icmS, icmT, icmV, icmW, icmX, iraA, iraB, laiE, lbtA, lbtB, lepA, lepB, letA, letS, lidA, lidL, ligA, lspC, lspD, lspE, lspF, lspG, lspH, lspI, lspJ, lspK, lspL, lspM, lvgA, IvhB10, IvhB11, lvhB2, lvhB3, lvhB4, lvhB5, lvhB6, lvhB7, lvhB8, lvhB9, lvhD4, mip, omp28, pilB, pi1C, pilD, pilE, pilE, pilM, pilN, pilO, pilP, pilQ, ralF, relA, rpoS, rtxA, sdbA, sdbB, sdbB-like, sdbC, sdcA, sdcB, sdeA/laiA, sdeB/laiB, sdeC/laiC, sdeD/laiF, sdhA, sdhB, sidA, sidB, sidC, sidD, sidE/laiD, sidE-like, sidF, sidG, sidH, vipA, vipD1, vipD2, vipD3, vipE, vipF, wipA, wipB, wipC, ylfA, ylfB

*Mycobacterium* (*M. tuberculosis*, *M. leprae*, *M. ulcerans*, *M. abscessus*, *M. africanum*, *M. avium*, *M. bovis*, *M. canettii*, *M. gilvum*, *M. indicus pranii*, *M. intracellulare*, *M. liflandii*, *M. marinum*, *M. massiliense*, *M. smegmatis*, *M. vanbaalenii*, *M. yongonense*)

adhD, ahpC, atf, caeA, cccD4, chp, chp1, cmaA2, ctpC, ctpV, cyp125, cyp143, ddrA, ddrB, devR/dosR, devS, drrC, eccA1, eccA2, eccA3, eccA5, eccB1, eccB2, eccB3, eccB4, eccB5, eccC2, eccC3, eccC4, eccCa1, eccCa5, eccCb1, eccCb5, eccD1, eccD2, eccD3, eccD5, eccE1, eccE2, eccE3, eccE5, ecf, eis, erp, espA, espB, espC, espD, espE, espF, espG1, espG2, espG3, espH, espI, espJ, espK, espL, espR, esxA, esxB, esxC, esxD, esxG, esxH, esxM, esxN, esxT, esxU, exiT, fad23, fad23, fadD13, fadD22, fadD26, fadD28, fadD29, fadD33, fadE14, fadE28, fadE29, fadE5, fbpA, fbpB, fbpC, fmt, fxbA, fxbBC, fxuA, fxuB, fxuC, fxuD, gap, gap-like, glnA1, gtf1, gtf2, gtf3, hbhA, hspX, icl, icl2, ideR, irtA, irtB, kasB, katG, kefB, leuD, lipF, lipR, lppx, lpqH, lpqY, lprG, lysA, mas, mbtA, mbtB, mbtC, mbtD, mbtE, mbtF, mbtG, mbtH, mbtH, mbtI, mbtJ, mbtK, mce1A, mce1B, mce1C, mce1D, mce1E, mce1F, mce2A, mce2B, mce2C, mce2D, mce2E, mce2F, mce3A, mce3B, mce3C, mce3D, mce3E, mce3F, mce4A, mce4B, mce4C, mce4D, mce4E, mce4F, mce5A, mce5B, mce5C, mce5D, mce5E, mce5F, mce6A, mce6B, mce6C, mce6D, mce6E, mce6F, mce7A, mce7B, mce7C, mce7D, mce7E, mce7F, mce8A, mce8B, mce8C, mce8D, mce8E, mce8F, mce9A, mce9B, mce9C, mce9D, mce9E, mce9F, mgtC, mlsA1, mlsA2, mlsB, mmaA4, mmpL10, mmpL11, mmpL3, mmpL4a, mmpL4b, mmpL7, mmpL8, mmpS4, mosR, mpa, mprA, mprB, mps1, mps2, mycP1, mycP2, mycP3, mycP4, mycP5, mymA, narG, narH, narI, narJ, narK2, narX, ndk, nuoG, ompA, pafA, panC, panD, papA1, papA2, papA3, papA5, pcaA, pe, PE_PGRS30, PE18, PE19, PE35, PE36, PE5, phoP, phoR, pknG, pks, pks1, pks15, pks15/1, pks2, pks4, plcB, plcC, plcD, PPE25, PPE26, PPE27, PPE4, PPE41, PPE68, PPE69, ppsA, ppsB, ppsC, ppsD, ppsE, proC, prrA, prrB, ptpA, purC, regX3, relA, rmlA, rmlB, rmt2, rmt3, rmt4, Rv0926, sadH, sap, sapM, secA2, senX3, sigA/rpoV, sigD, sigE, sigF, sigH, sigL, sigM, sodA, sodC, stf0, sugA, sugB, sugC, tesA, tgs4, trpD, whiB3, zmp1

*Mycoplasma* (*M. agalactiae*, *M. capricolum*, *M. gallisepticum*, *M. genitalium*, *M. hyopneumoniae*, *M. mobile*, *M. mycoides*, *M. penetrans*, *M. pneumoniae*, *M. pulmonis*, *M. synoviae*)

hlyA, hmw1, hmw2, hmw3, lppT, mvsp, nuc, orf6/MgpC/crmA, p1/MgPa/gapA, p102, p146, p159, p200, p216, p29, p30/p32, p35, p40, p48, p50, p65, p65, p97, pdhB, pvpA, tuf, vamp, vlh, vmm, vsa

*Neisseria* (*N. gonorrhoeae*, *N. meningitidis*, *N. lactAmia*)

app, ctrA, ctrB, ctrC, ctrD, exbB, exbD, farA, farB, fbpA, fbpB, fbpC, fetA/frpB, fHbp, frpA, frpC, hmbR, hpuA, hpuB, iga, katA, kdtA/waaA, lbpA, lbpB, lgtA, lgtB, lgtC, lgtD, lgtE, lgtF, lgtG, lgtH, lipA, lipB, lptA, lst, mntA, mntB, mntC, msrA/B(pilB), mtrC, mtrD, mtrE, mynA/sacA, mynB/sacB, mynC/sacC, mynD/sacD, nadA, narE, nspA, opa, opc, pilC, pilD, pilE, pilF, pilG, pilH, pilI, pia, pilK, pilM, pilN, pilO, pilP, pilQ, pilS, pilT, pilT2, pilU, pilV, pilW, pilX, pilZ, porA, porB, recN, rfaC, rfaF, rfaK, siaA/synA, siaB/synB, siaC/synC, siaD/synD, synE, tbpA, tbpB, tonB

*Pseudomonas* (*P. aeruginosa*, *P. entomophila*, *P. fluorescens*, *P. mendocina*, *P. putida*, *P. stutzeri*, *P. syringae*)

acsA, acsB, acsC, acsD, ahlI, ahlR, alg44, alg8, algA, algC, algD, algE, algF, algG, algI, algJ, algK, algL, algP/algR3, algQ, algR, algU, algW, algX, algZ, aprA, argD, argK, avrB2, avrB3, avrB4-1, avrB4-2, avrD1, avrE1, avrPto1, avrRpm1, avrRps4, cbrA, cbrB, cbrC, cbrD, cfa1, cfa2, cfa3, cfa4, cfa5, cfa6, cfa7, cfa8, cfa9, cfl, chpA, chpB, chpC, chpD, chpE, clpV1, cmaA, cmaB, cmaC, cmaD, cmaE, cmaT, cmaU, corP, corR, cysC1, dcd2, exoS, exoT, exoU, exoY, exsA, exsB, exsC, exsD, exsE, fhaI, fimT, fimU, fimV, flaG, fleN, fleQ, fleR, fleS, flgA, flgB, flgC, flgD, flgE, flgF, flgG, flgH, flgI, flgJ, flgK, flgL, flgM, flgN, flhA, flhB, flhF, fliA, fliC, fliD, fliE, fliF, fliG, fliH, fliI, fliJ, fliK, fliL, fliM, fliN, fliO, fliP, fliQ, fliR, fliS, fliT, fptA, fpvA, fyuA, gacA, gacS, hcnA, hcnB, hcnC, hcp1, hdtS, hopA1, hopAA1, hopAA1', hopAA1-1, hopAA1-2, hopAB1, hopAB2, hopAB3', hopAC::ISPsy5, hopAC1, hopAD1, hopAE1, hopAF1, hopAG::ISPssy, hopAG1, hopAH1, hopAH2, hopAH2-1, hopAH2-2, hopAI1, hopAI1', hopAJ1, hopAJ2, hopAK1, hopAM1-1, hopAM1-2, hopAN1, hopAO1, hopAP1, hopAQ1, hopAS1, hopAS1', hopAT1, hopAT1', hopAU1, hopAV1, hopAW1, hopB1, hopC1, hopD::IS52, hopD1, hopE1, hopF2, hopF3, hopG1, hopH1, hopI1, hopJ1, hopK1, hopL1, hopM1, hopM1', hopN1, hopO1-1, hopO1-3', hopP1, hopP1-2, hopQ1, hopQ1-1, hopQ1-2, hopR1, hopS1', hopS2, hopT1-1, hopT1-2, hopT2, hopU1, hopV1, hopW1-1, hopW1-2, hopX1, hopY 1, hopZ3, hrcC, hrcJ, hrcN, hrcQa, hrcQb, hrcR, hrcS, hrcT, hrcU, hrcV, hrpA1, hrpA2, hrpB, hrpD, hrpE, hrpF, hrpG, hrpJ, hrpK1, hrpL, hrpO, hrpP, hrpQ, hrpR, hrpS, hrpT, hrpV, hrpW1, hrpZ1, icmF1, irp1, irp2, irp3, irp4, irp5, lasA, lasB, lasI, lasR, motA, motB, motC, motD, motY, mucA, mucB, mucC, mucD, mucE, mucP, pchA, pchB, pchC, pchD, pchE, pchF, pchG, pchH, pchI, pchR, per1, per2, per3, per4, perD, perG, perH, perR, perV, phzA1, phzA2, phzB1, phzB2, phzC2, phzC2, phzD1, phzD2, phzE1, phzE2, phzF1, phzF2, phzG1, phzG2, phzH, phzM, phzS, pilA, pilB, pilC, pilD, pilE, pilF, pilG, pilH, pilI, pilJ, pilK, pilM, pilN, pilO, pilP, pilQ, pilR, pilS, pilT, pilU, pilV, pilW, pilX, pilY1, pilY2, pilZ, plcB, plcH, plcN, pldA, popB, popD, popN, ppkA, pppA, prpL, pscB, pscC, pscD, pscE, pscF, pscG, pscH, pscI, pscJ, pscK, pscL, pscN, pscO, pscP, pscQ, pscR, pscS, pscT, pscU, pvdA, pvdD, pvdE, pvdF, pvdG, pvdH, pvdI, pvdJ, pvdL, pvdM, pvdN, pvdO, pvdP, pvdQ, pvdS, pvdY, rhlA, rhlB, rhlC, rhlI, rhlR, shcA, shcE, shcF, shcM, shcN, shcS1, shcS2, shcV, sypA, sypB, sypC, syrB1, syrB2, syrC, syrD, syrE, syrF, syrP, toxA, vgrG1, ybtA, ybtP, ybtQ

*Salmonella* (*S. typhimurium*, *S. typhi*, *S. enterica*)

avrA, bcfA, bcfB, bcfC, bcfD, bcfE, bcfF, bcfG, cdtB, csgA, csgB, csgC, csgD, csgE, csgF, csgG, fimA, fimC, fimD, fimF, fimH, fimI, fimW, fimY, fimZ, gogB, hilA, hilC, hilD, iacP, iagB, invA, invB, invC, invE, invF, invG, invH, invI, invJ, lpfA, lpfB, lpfC, lpfD, lpfE, mgtB, mgtC, mig-14, mig-5, misL, orgA, orgB, orgC, pefA, pefB, pefC, pefD, pegA, pegB, pegC, pegD, phoP, phoQ, pipB, pipB2, pltA, pltB, prgH, prgI, prgJ, prgK, ratB, rck, safA, safB, safC, safD, sefA, sefB, sefC, sefD, shdA, sicA, sicP, sifA, sifB, sinH, sipA, sipB, sipC, sipD, slrP, sodCI, sopA, sopB/sigD, sopD, sopD2, sopE, sopE2, spaO, spaP, spaQ, spaR, spaS, spiC/ssaB, sprB, sptP, spvA, spvB, spvC, spvD, spvR, ssaC, ssaD, ssaE, ssaG, ssaH, ssaI, ssaJ, ssaK, ssaL, ssaM, ssaN, ssaO, ssaP, ssaQ, ssaR, ssaS, ssaT, ssaU, ssaV, sscA, sscB, sseA, sseB, sseC, sseD, sseE, sseF, sseG, sseI/srfH, sseJ, sseK1, sseK2, sseL, sspH1, sspH2, ssrA, ssrB, staA, staB, staC, staD, staE, staF, staG, stbA, stbB, stbC, stbD, stbE, stcA, stcB, stcC, stcD, stdA, stdB, stdC, steA, steB, steC, steD, steE, steF, stfA, stfC, stfD, stfE, stfF, stfG, stgA, stgB, stgC, stgD, sthA, sthB, sthC, sthD, sthE, stiA, stiB, stiC, stiH, stjB, stjC, stkA, stkB, stkC, stkD, stkE, stkF, stkG, tcfA, tcfB, tcfC, tcfD, tviA, tviB, tviC, tviD, tviE, vexA, vexB, vexC, vexD, vexE

*Shigella* (*S. dysenteriae, S. flexneri, S. boydii* and *S. sonnei*)
entA, entB, entC, entD, entE, entF, fepA, fepB, fepC, fepD, fepG, gspC, gspD, gspE, gspF, gspG, gspH, gspI, gspJ, gspK, gspL, gspM, gtr, gtrA, gtrB, icsA/virG, icsB, icsP/sopA, ipaA, ipaB, ipaC, ipaD, ipaH, ipaH1.4, ipaH2.5, ipaH4.5, ipaH7.8, ipaH9.8, ipgA, ipgB1, ipgB2, ipgC, ipgD, ipgE, ipgF, iroB, iroC, iroD, iroE, iroN, iucA, iucB, iucC, iucD, iutA, msbB2, mxiA, mxiC, mxiD, mxiE, mxiG, mxiH, mxiI, mxiJ, mxiK, mxiL, mxiM, mxiN, ospB, ospC1, ospC2, ospC3, ospC4, ospD1, ospD2, ospD3, ospE1, ospE2, ospF, ospG, pic, sepA, set1A, set1B, shuA, shuS, shuT, shuU, shuV, shuW, shuX, shuY, sigA, sitA, sitB, sitC, sitD, spa13, spa15, spa24, spa29, spa32, spa33, spa40, spa47, spa9, stxA, stxB, virA, virB, virF, virK

*Staphylococcus* (*S. aureus, S. epidermidis, S. haemolyticus, S. saprophyticus*)
atl, clfA, clfB, cna, coa, eap/map, ebh, ebp, efb, esaA, esaB, esaC, essA, essB, essC, esxA, esxB, eta, etb, etc, etd, fnbA, fnbB, geh, hlb, hld, hlgA, hlgB, hlgC, hly/hla, hysA, icaA, icaB, icaC, icaD, icaR, lip, lukD, lukE, lukF-like, lukF-PV, lukM, lukS-PV, nuc, sak, sdrC, sdrD, sdrE, sdrF, sdrG, sdrH, sea, seb, sec, sed, see, seg, seh, sei, sej, selk, sell, selm, seln, selo, selp, selq, selr, selu, set1, set10, set11, set12, set13, set14, set15, set16, set17, set18, set19, set2, set20, set21, set22, set23, set24, set25, set26, set3, set30, set31, set32, set33, set34, set35, set36, set37, set38, set39, set4, set40, set5, set6, set7, set8, set9, spa, splA, splB, splC, splD, splE, splF, sspA, sspB, sspC, tsst, yent1, yent2

*Streptococcus* (*S. pyogenes, S. agalactiae, S. gordonii, S. mutans, S. pneumoniae, S. sanguinis, S. suis, S. thermophiles*)
acpC, alp2, bca, cba, cbpD, cbpG, cfa/cfb, cpa, cpbA, cppA, cshA, cshB, cylA, cylB, cylD, cylE, cylF, cylG, cylI, cylJ, cylK, cylX, cylZ, emm, endoS, enn, eno, epf, fbaA, fbp54, fbsA, fbsB, gbpA, gbpC, gbpD, grab, gspB, gtfB, gtfC, gtfD, gffG, hsa, htrA/degP, hyl, hylA, hylB, hylP, hysA, ideS/mac, iga, lmb, lytA, lytB, lytC, mf/spd, mf2, mf3, mf4, mrp, mrp, nanA, pavA, pce/cbpE, piaA, piuA, plr/gapA, ply, prtF2, prtF2, psaA, pspA, pspC/cbpA, rib, rrgA, rrgB, rrgC, sagA, sclA, sclB, scpA/scpB, sda, sdn, sfbI/prtF 1, sfbII/sof, sfbX, sic, sip, ska, slaA, slo, slrA, sly, smeZ, spaP/pac, speA, speB, speC, speG, speH, speI, speJ, speK, speL, speM, spyA, srtA, srtB, srtC, srtD, ssa, sspA, sspB, tig/ropA, wapA, zmpB, zmpC

*Vibrio* (*V. cholerae, V. parahaemolyticus, V. vulnificus, V fischeri, V. parahaemolyticus*)
ace, acfA, acfB, acfC, acfD, cheA, cheB, cheR, cheV, cheW, cheY, cheZ, cpsA, cpsB, cpsC, cpsD, cpsE, cpsF, cpsG, cpsH, cpsI, cpsJ, cqsA, ctxA, ctxB, epsC, epsE, epsF, epsG, epsH, epsI, epsJ, epsK, epsL, epsM, epsN, filM, flaA, flaB, flaC, flaD, flaE, flaG, flaI, flgA, flgB, flgC, flgD, flgE, flgF, flgG, flgH, flgI, flgJ, flgK, flgL, flgM, figN, flhA, flhB, flhF, flhG, fliA, fliD, fliE, fliF, fliG, fliH, fliI, fliJ, fliK, fliL, fliN, fliO, fliP, fliQ, fliR, fliS, flrA, flrB, flrC, gspD, hap/vvp, hasR, hcp-1, hcp-2, hlyA, hp1, hutA, hutR, irgA, luxS, motA, motB, motX, motY, mshA, mshB, mshC, mshD, mshE, mshF, mshG, mshH, mshI, mshJ, mshK, mshL, mshM, mshN, nanH, pilA, pilB, pilC, pilD, rmlA, rmlB, rmlC, rmlD, rtxA, rtxB, rtxC, rtxD, sycN, tcpA, tcpB, tcpC, tcpD, tcpE, tcpF, tcpH, tcpI, tcpJ, tcpN/toxT, tcpP, tcpQ, tcpR, tcpS, tcpT, tdh, tlh, tyeA, vasA, vasB, vasC, vasD, vasE, vasF, vasG, vasH, vasI, vasJ, vasK, vcrD, vcrD2, vcrG, vcrH, vcrR, vcrV, vctA, vctC, vctD, vctG, vctP, vgrG-1, vgrG-2, vgrG-3, vibA, vibB, vibC, vibD, vibE, vibF, vibH, virF, virG, viuA, viuB, viuC, viuD, viuG, viuP, vopA, vopB, vopC, vopD, vopL, vopN, vopQ, vopR, vopS, vopT, vscA, vscB, vscC, vscC2, vscD, vscF, vscG, vscH, vscI, vscJ, vscK, vscL, vscN, vscN2, vscO, vscP, vscQ, vscR, vscS, vscT, vscU, vscX, vscY, vvhA, vxsC, wbfB, wbfC, wbfT, wbfU, wbfV/wcvB, wbfY, wbjD/wecB, wbuB, wcaJ, wecA, wecC, wza, wzb, wzc, zot

*Yersinia* (*Y. pestis, Y pseudotuberculosis, Y enterocolitica*)
acpY, ail, caf1, cnf, flgA, flgB, flgC, flgD, flgE, flgF, flgG, flgH, flgI, flgJ, flgK, flgL, flgM, figN, flhA, flhB, flhC, flhD, flhE, fliA, fliB, fliG, fliD, fliE, fliF, fliG, fliH, fliI, fliJ, fliK, fliL, fliM, fliN, fliO, fliP, fliQ, fliR, fliS, fliT, fliZ, inv, irp1, irp2, lcrE/yopN, lcrG, lcrO/yscI, lcrQ/yscM, lcrR, lcrV, pilD, pilL, pilM, pilN, pilO, pilP, pilQ, pilR, pilS, pilU, pilV, pilW, pla, psaA, psn/fyuA, sycB, sycD/lcrH, sycN, tyeA, virF/lcrF, virG/yscW, yadA, ybtA, ybtE, ybtP, ybtQ, ybtS, ybtT, ybtU, ybtX, ylpB/yscJ, ymt, yopB, yopD, yopE, yopH, yopJ/yopP, yopM, yopO/ypkA, yopR/yscH/lcrP, yopT, yplA, ypmA, ysaC, ysaE, ysaH, ysaI, ysaJ, ysaK, ysaN, ysaQ, ysaR, ysaS, ysaT, ysaU, ysaV, ysaW, yscA, yscB, yscC, yscD, yscE, yscF, yscG, yscK, yscL, yscN, yscO, yscP, yscQ, yscR, yscS, yscT, yscU, yscV/lcrD, yscX, yscY, yspB, yspC, yspD, ysrR, ysrS, yst1C, yst1E, yst1F, yst1G, yst1H, yst1I, yst1J, yst1K, yst1L, yst1M, yst1O, yst1S In particular embodiments herein, the microorganism is a *Listeria* species, such as *L. monocytogenes*. In specific examples, the target gene of *Listeria* is selected from inlA, inlB, plcA, hylA, actA, plcB, ssrB, ssrA and/or iap. In particular, for genus-specific identification of *Listeria*, ssrB, ssrA and/or iap can be selected. For species-specific detection of *L. monocytogenes*, inlA, inlB, plcA, hylA, actA, and/or plcB can be selected.

VI. Samples

Any biological or environmental specimen that may contain (or is known to contain or is suspected of containing) a target microorganism can be tested using the methods provided herein to determine if a target microorganism is present. Once a sample has been obtained, the sample can be used directly, concentrated (for example by centrifugation or filtration), purified, liquefied, diluted in a fluid, or combinations thereof.

Biological samples obtained from a subject (such as a mammal (e.g., human), fish, or bird) and include genomic DNA, RNA (including mRNA), protein, or combinations thereof. Examples include a tissue biopsy, fine needle aspirate, bronchoalveolar lavage, pleural fluid, spinal fluid, saliva, sputum, surgical specimen, lymph node fluid, ascites fluid, peripheral blood (such as serum or plasma), urine, saliva, buccal swab, and autopsy material. Techniques for acquisition of such samples are well known in the art (for example see Schluger et al. *J. Exp. Med.* 176:1327-33, 1992, for the collection of serum samples). Serum or other blood fractions can be prepared in the conventional manner. Samples can also include fermentation fluid and tissue culture fluid.

Environmental samples that can be tested with the disclosed methods include those obtained from an environmental media, such as water, air, soil, dust, wood, plants or food.

In one example the sample to be tested with the disclosed methods is a food sample, such as a meat, dairy, fruit, food product, or vegetable sample. For example, using the methods provided herein, adulterants in food products can be detected, such as a pathogen or toxin or other harmful product.

In other examples, a sample includes a control sample, such as a sample known to contain or not contain a particular target microorganism.

The following examples are provided to illustrate certain particular features and/or embodiments. These examples should not be construed to limit the disclosure to the particular features or embodiments described.

EXAMPLES

The organism *Listeria monocytogenes* grows very slowly compared to other types of bacteria. Previously, the inventors developed a Custom *Listeria* Enrichment Media (CLEM). This media was generated by inoculating the *L. monocytogenes* strain EGD-e into tryptic soy broth (TSB) and allowing the culture to grow for a short period of time. The bacteria were removed by filtration and the spent media (CLEM) was used for downstream experiments and bacterial growth. While this media allowed for 4× the growth in 5-7 hours compared to commercial formulations, it was determined that soluble DNA was present in the CLEM. This DNA caused technical challenges because it generated a false positive polymerase chain reaction (PCR) result and it reduced the sensitivity of final detection by PCR.

To solve this problem, the inventors constructed an *L. monocytogenes* strain deficient in two gene markers and an accompanying PCR assay for the detection of *Listeria* species and *Listeria monocytogenes* strains. The following Examples describe (1) the design and generation of an *L. monocytogenes* EGD-e strain deficient in two gene markers for use as the PCR target; (2) the production of media from the new strain; and (3) verification of enrichment performance and PCR compatibility. The new bacterial strain, *L. monocytogenes* EGD-e JH11 (-actA, -ssrB) is used to make enrichment media that is referred to herein as "CLEM-4." CLEM-4 does not generate false positive PCR results because the PCR signature has been removed from the bacteria and the resulting media. This same approach is applicable to any microorganism of interest.

Example 1

Generation of an *L. monocytogenes* Strain with Mutations in actA

This example describes the generation of an *L. monocytogenes* strain designated EGD-e JH2, which contains four mutations in the actA gene. The actA gene is specific for *L. monocytogenes* (i.e., actA is not present in other *Listeria* species).

The actA gene sequence was downloaded from the NCBI database (GENBANK™ Accession No. FJ947113.1) and a PCR primer probe set was designed using the Integrated DNA technologies website. An additional probe was designed with a four nucleotide change; this was a mutated form of the wild-type sequence. To generate the plasmid construct, restriction enzymes were added to the primers used to generate the PCR amplicon with the mutation. These primers were used to amplify the gene from genomic DNA. The PCR product was digested with restriction enzymes, and cloned into the temperature sensitive suicide shuttle vector pKSV7. The product was cloned into *E. coli* DH5 alpha cells and plasmid DNA was extracted. The plasmid containing the gene mutation was then electroporated into *L. monocytogenes* EGD-e. A stable mutation was generated in *L. monocytogenes* EGD-e by (1) forcing the plasmid to integrate into the chromosome, and (2) excision of the plasmid sequence, removing the wild-type gene sequence and leaving the sequence with the silent mutations. Individual colonies were screened for the loss of the wild-type and the gain of the mutations using real time PCR. Once a putative mutant was identified, the actA gene was sequenced to verify the presence of the mutations. This stain was designated *L. monocytogenes* EGD-e JH2 (-actA). The wild-type and mutant target sequences, as well as the primer and probe sequences that accompany the strains, are provided below. The four nucleotide positions that are mutated are shown in bold underline.

actA wild type target sequence:

```
actA wild type target sequence:
                                          (SEQ ID NO: 1)
CGCACCGGCTCTGATAAGTGACAT actA silent mutation target sequence (JH2):
                                          (SEQ ID NO: 2)
CGCACGTGCTTTTATAAGTGACAT (SEQ ID NO: 3)
Forward Primer - AAAACACTCAAGAAATGCGGG (SEQ ID NO: 4)
Reverse Primer - CTGTGATGGATTCTTAAATGGCG (SEQ ID NO: 5)
Probe - CGCACCGGCTCTGATAAGTGACAT
```

Example 2

Generation of an *L. monocytogenes* Strain with Mutations in ssrB

Mutation of the actA gene enables detection of bacteria at the species level (*L. monocytogenes*). This example describes an *L. monocytogenes* strain containing mutations in a second gene (ssrB), which will enable detection of bacteria at the genus level (*Listeria*).

A second series of mutations were designed and constructed in *L. monocytogenes* EGD-e JH2 (-actA) strain. Specifically, a seven nucleotide mutation was designed for the ssrB gene, according to the same protocol described for actA in Example 1. Sequencing verified the mutations in the ssrB gene. The new strain was designated *L. monocytogenes* EGD-e JH11 (-actA, -ssrB). The wild-type and mutant target sequences, as well as the primer and probe sequences that accompany the strains, are provided below. The seven nucleotide positions that are mutated are shown in bold underline.

```
ssrB wild type target sequence:
                                          (SEQ ID NO: 6)
AGAGTCCGGTTATTCGATTGTTCC
```

-continued ssrB silent mutation sequence:
(SEQ ID NO: 7)
AGAATCGGGCTACTCCATCGTACC (SEQ ID NO: 8)
Forward Primer - TCATGATCCACTAAGAACGCG (SEQ ID NO: 9)
Reverse Primer - ACACCGATAAGTACTTTTGCG (SEQ ID NO: 10)
Probe - AGAGTCCGGTTATTCGATTGTTCC Example 3

Preparation and Evaluation of Custom *Listeria* Enrichment Media and Gene Matched PCR Assay This example provides the protocol for generating Custom *Listeria* Enrichment Media (CLEM) using the mutant *L. monocytogenes* strains described in Example 1 and Example 2. This example further describes gene-matched PCR assays for detection of *L. monocytogenes* strains (species level assay) and other *Listeria* species (genus level assay).

CLEM Methodology:

1) Streak plate *Listeria monocytogenes* onto brain heart infusion (BHI) agar (Teknova, Hollister, Calif.). CLEM-2 is generated using *L. monocytogenes* strain EGD-e (ATCC, Manassas, Va.); CLEM-3 is generated using *L. monocytogenes* strain EGD-e JH2 (see Example 1); and CLEM-4 is generated using *L. monocytogenes* strain EGD-e JH11 (see Example 2).

2) Incubate at 37° C. until well-defined single colonies are visible (18 to 24 hours).

3) Inoculate 12 mL of BD broth (Becton, Dickinson and Company, Sparks, Md.) in a 50 mL FALCON™ tube with a single *L. monocytogenes* colony.

4) Incubate at 37° C. at 100 rotations per minute (rpm) in a horizontal position overnight.

5) Pre-warm 99 mL BD Bacto Tryptic Soy Broth (TSB) without dextrose to 37° C. using ten 500 mL glass flasks.

6) Inoculate each flask with 1 mL of overnight culture; the optical density (OD) of the culture should be between 0.4 and 0.6 (measured at 600 nm on a spectrophotometer).

7) Incubate at 37° C. at 200 rpm until the OD is between 0.35 and 0.44 (approximately 3 to 4 hours).

8) Filter contents of all flasks into a sterile glass media bottle using a sterile filter (0.22 μm Corning PES bottle-top filter unit, Corning, Inc., Corning, N.Y.).

9) Store CLEM refrigerated and protected from light.

Performance of CLEM-3:

To evaluate the *Listeria* enrichment capability of CLEM-3, growth of *L. monocytogenes* strain ATCC 15313 in TSB, CLEM-2 and CLEM-3 was compared. *L. monocytogenes* ATCC 15313 (45 CFU) was inoculated into each media and incubated for seven hours. Following the seven hour enrichment period, the fold change in CFU was calculated. As previously determined, use of CLEM-2 led to significantly greater enrichment than TSB (176-fold compared with 359-fold increase in *L. monocytogenes*). CLEM-3 performed as well or better than CLEM-2, resulting in a 391-fold increase (see FIG. 1).

PCR Assays:

To confirm that CLEM-3 is negative for the *L. monocytogenes* DNA signature, PCR was performed using the actA mutation-specific (species level) primers (SEQ ID NOs: 3 and 4). As shown in FIG. 2, CLEM-2 was positive for the *L. monocytogenes* DNA signature, while CLEM-3 was negative. Further studies determined that the species level PCR assay was capable of detecting as few as 5-7 bacterial cells or 25 fg of purified DNA.

PCR assays performed using the ssrB mutation-specific (genus level) primers (SEQ ID NOs: 8 and 9) determined that the genus level PCR assay was capable of detecting as little as 100 fg of purified DNA.

CLEM Additives:

Further studies were carried out to determine whether the enrichment capability of CLEM could be further enhanced with additives. CLEM-3 with the following additives was produced: 2% L-glutamine, 0.25 mg/L biotin, 0.02% Tween-20 and 2.5 g/L glucose. TSB, CLEM-3 (without additives) and CLEM-3 with additives were compared. Each media was inoculated with 47 CFU of *L. monocytogenes* ATCC 15313. After a seven hour enrichment period, fold enrichment was calculated. The results demonstrated that CLEM-3 with additives produced a greater fold-change (on average) than CLEM-3 without additives, although variability was greater among the replicates for CLEM-3 with additives, as compared to TSB and CLEM-3 without additives (FIG. 3).

Example 4

Optimization of the Gene-Matched PCR Assay

This example describes strategies to optimize the gene-matched PCR assay disclosed herein.

When rapid enrichment media is generated, excess DNA remains in the media after it is filtered to remove bacterial cells. The excess DNA can increase the consumption of PCR primer/probe reagents and potentially lead to degradation of PCR sensitivity. Strategies to minimize the potential effect of the excess DNA are described below.

PCR forward primers can be designed to bind the region of DNA corresponding to the region containing silent mutations in the modified gene, but not bind the excess DNA that remains in the spent enrichment media.

In addition, different PCR reagent concentrations can be assessed to reduce PCR reagent consumption.

Other methods of PCR optimization are well-known to those of skill in the art. Specific examples include, but are not limited to, using tangential flow devices in reverse and using ultrasonic energy to sheer DNA.

Example 5

Growth Media

The type of growth media used to generate spent enrichment media is selected based on, for example, the type of microorganism that is suspected of being present in a sample to be tested. Exemplary growth media that can be used in the compositions and methods disclosed herein include the following components (but may also include additional ingredients):

Tryptic Soy Broth without Dextrose
Peptone
Sodium Chloride
Dipotassium Phosphate
Tryptic Soy Broth with Dextrose
Peptone
Dextrose
Sodium Chloride
Dipotassium Phosphate
Brain Heart Infusion Brain Heart, Infusion from (Solids)
Peptic Digest of Animal Tissue
Pancreatic Digest of Casein
Sodium Chloride
Glucose
Disodium Hydrogen Phosphate
Luria-Bertani
Tryptone
Yeast extract
Sodium chloride
Nutrient Broth
Beef extract
Peptone
Peptone Buffered Water
Peptone
Sodium chloride
Disodium Phosphate
Monopotassium Phosphate Any growth media, including any of the growth media listed above, can be supplemented with one or more additional components, including, but not limited to blood (such as bovine or sheep blood), beef extract, M9 salts and casamino acids.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

The invention claimed is:

1. A spent enrichment growth media for the growth of a species of microorganism, the spent enrichment growth media comprising:

cellular debris and nucleic acids from a modified microorganism of a species, the nucleic acids comprising at least one target gene comprising a plurality of silent mutations, wherein the at least one target gene comprises an actA gene and the actA gene comprising a plurality of silent mutations comprises SEQ ID NO: 2, wherein the at least one target gene comprises an ssrB gene and the ssrB gene comprising a plurality of silent mutations comprises SEQ ID NO: 7, or both, wherein the modified microorganism of the species has been removed from the spent enrichment media; and microorganisms of the species comprising the at least one target gene without the plurality of silent mutations.

2. A kit for detecting a microorganism, comprising:

the spent enrichment media of claim 1; and a pair of oligonucleotide primers that permit amplification of the at least one target gene that does not have the plurality of silent mutations.

3. The spent enrichment growth media of claim 1, wherein the spent enrichment growth media is lyophilized.

4. The spent enrichment growth media of claim 1, wherein the spent enrichment growth media further comprises one or more additives selected from the group consisting of L-glutamine, biotin, Tween-20, glucose, KC1, norepinephrine, and L-alanine.

5. The spent enrichment growth media of claim 1, wherein the species is *Listeria* monocytogenes.

6. The spent enrichment growth media of claim 1, wherein the at least one target gene further comprises inlA, inlB, plcA, hylA, actA, plcB, ssrB, ssrA or iap.

7. The spent enrichment growth media of claim 1, wherein the at least one target gene comprises the actA gene and the actA gene comprising a plurality of silent mutations comprises SEQ ID NO: 2.

8. The spent enrichment growth media of claim 1, wherein the at least one target gene comprises the ssrB gene and the ssrB gene comprising a plurality of silent mutations comprises SEQ ID NO: 7.

9. A spent enrichment growth media generated by a method comprising:
inoculating a suitable growth media with a modified microorganism comprising a plurality of silent mutations in at least one target gene, wherein the at least one target gene comprises an actA gene and the actA gene comprising a plurality of silent mutations comprises SEQ ID NO: 2, the at least one target gene comprises an ssrB gene and the ssrB gene comprising a plurality of silent mutations comprises SEQ ID NO: 7, or both;
allowing the modified microorganism to grow in the media for a selected period of time; and
filtering the media to remove cells of the modified microorganism, thereby producing spent enrichment media.

10. The spent enrichment growth media of claim 9, the spent enrichment growth media further comprises a culture of a second microorganism of the same species as the modified microorganism, the second microorganism comprising the at least one target gene without the plurality of silent mutations.

11. The spent enrichment growth media of claim 9, wherein the spent enrichment growth media is suitable for the growth of a *Listeria* species,
wherein the modified microorganism is a *L. monocytogenes* bacterium comprising the plurality of silent mutations in at least one target gene,
wherein the *L. monocytogenes* bacterium comprising the plurality of silent mutations in at least one target gene is allowed to grow for a period of time sufficient to achieve an $OD_{600}$ of about 0.3 to about 0.5, and
wherein the filtered media is sufficient for growth of a *Listeria* species.

12. The spent enrichment growth media of claim 9, wherein the at least one target gene further comprises inlA, inlB, plcA, hylA, actA, plcB, ssrB, ssrA or iap.

13. The spent enrichment growth media of claim 9, wherein the at least one target gene comprises the actA gene and the actA gene comprising a plurality of silent mutations comprises SEQ ID NO: 2.

14. The spent enrichment growth media of claim 9, wherein the at least one target gene comprises the ssrB gene and the ssrB gene comprising a plurality of silent mutations comprises SEQ ID NO: 7.

15. A kit for detection of *Listeria* species, comprising:
the spent enrichment growth media of claim 9; and
a pair of oligonucleotide primers, wherein at least one of the oligonucleotide primers comprises the nucleotide sequence of SEQ ID NO: 3, SEQ ID NO: 4, SEQ ID NO: 8 or SEQ ID NO: 9.

16. The kit of claim 15, further comprising an oligonucleotide probe comprising the sequence of SEQ ID NO: 5 or SEQ ID NO: 10.

17. A method for producing the spent enrichment growth media of claim 1, the method comprising:
inoculating a suitable growth media with a modified microorganism comprising a plurality of silent mutations in at least one target gene;
allowing the modified microorganism to grow in the media for a selected period of time;
filtering the media to remove cells of the modified microorganism, thereby producing spent enrichment growth media; and
inoculating the spent enrichment media with microorganisms of the species comprising the at least one target gene without the plurality of silent mutations.

18. The method of claim 17, wherein the modified microorganism is an *L. monocytogenes* bacterium of comprising a plurality of silent mutations in at least one target gene, wherein the selected period of time is sufficient to achieve an $OD_{600}$ of about 0.3 to about 0.5, and wherein the spent enrichment growth media improves the growth of a *Listeria* species.

* * * * *

SEQUENCE LISTING

```
<160> NUMBER OF SEQ ID NOS: 10

<210> SEQ ID NO 1
<211> LENGTH: 24
<212> TYPE: DNA
<213> ORGANISM: Listeria monocytogenes

<400> SEQUENCE: 1
cgcaccggct ctgataagtg acat                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 2
cgcacgtgct tttataagtg acat                                          24

<210> SEQ ID NO 3
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 3
aaaacactca agaaatgcgg g                                             21

<210> SEQ ID NO 4
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 4
ctgtgatgga ttcttaaatg gcg                                           23

<210> SEQ ID NO 5
<211> LENGTH: 24
<212> TYPE: DNA
<213> ORGANISM: Artificial Sequence
<220> FEATURE:
<223> OTHER INFORMATION: Synthetic polynucleotide
```

```
<400> SEQUENCE: 5
cgcaccggct ctgataagtg acat                                              24

<210> SEQ ID NO 6
<211> LENGTH: 24
<212> TYPE: DNA
<213> ORGANISM: Listeria monocytogenes

<400> SEQUENCE: 6
agagtccggt tattcgattg ttcc                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 7
agaatcgggc tactccatcg tacc                                              24

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
tcatgatcca ctaagaacgc g                                                 21

<210> SEQ ID NO 9
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 9
acaccgataa gtacttttgc g                                                 21

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
agagtccggt tattcgattg ttcc                                              24
```